US012623076B2

(12) United States Patent
Dinsmoor et al.

(10) Patent No.: US 12,623,076 B2
(45) Date of Patent: May 12, 2026

(54) ELECTRODE SELECTION BASED ON IMPEDANCE FOR SENSING OR STIMULATION

(71) Applicant: Medtronic, Inc., Minneapolis, MN (US)

(72) Inventors: David A. Dinsmoor, North Oaks, MN (US); Juan G. Hincapie, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 283 days.

(21) Appl. No.: 18/260,910

(22) PCT Filed: Feb. 18, 2022

(86) PCT No.: PCT/US2022/070735
§ 371 (c)(1),
(2) Date: Jul. 10, 2023

(87) PCT Pub. No.: WO2022/183172
PCT Pub. Date: Sep. 1, 2022

(65) Prior Publication Data
US 2024/0075286 A1     Mar. 7, 2024

Related U.S. Application Data

(60) Provisional application No. 63/152,915, filed on Feb. 24, 2021.

(51) Int. Cl.
*A61N 1/36*     (2006.01)
*A61N 1/04*     (2006.01)
*A61N 1/08*     (2006.01)

(52) U.S. Cl.
CPC ......... *A61N 1/3603* (2017.08); *A61N 1/0476* (2013.01); *A61N 1/08* (2013.01); *A61N 1/36139* (2013.01); *A61N 2001/083* (2013.01)

(58) Field of Classification Search
None
See application file for complete search history.

(56) References Cited

U.S. PATENT DOCUMENTS 8,116,872 B2     2/2012  Tehrani et al.
2013/0006324 A1*  1/2013  Bradley .............. A61N 1/0551
                                                  607/45

(Continued)

OTHER PUBLICATIONS

International Search Report and Written Opinion of International Application No. PCT/US2022/070735 dated Jun. 1, 2022, 13 pp.

(Continued)

*Primary Examiner* — Michael W Kahelin
(74) *Attorney, Agent, or Firm* — Shumaker & Sieffert, P.A.

(57)     ABSTRACT

An example medical device includes processing circuitry configured to determine an electrode impedance value for each of one or more electrodes of a lead coupled to the medical device, identify one or more of the electrodes having electrode impedance values that are greater than electrode impedance values of other electrodes of the lead, from the identified one or more electrodes, determine a recommendation of electrodes to use for sensing a signal, and output information indicative of the recommendation.

21 Claims, 9 Drawing Sheets

(56) References Cited

U.S. PATENT DOCUMENTS

| | | | |
|---|---|---|---|
| 2014/0276925 A1* | 9/2014 | Alves | A61B 17/3401 |
| | | | 606/129 |
| 2015/0173636 A1 | 6/2015 | Mokelke et al. | |
| 2016/0157769 A1* | 6/2016 | Min | G16H 20/40 |
| | | | 600/547 |
| 2018/0256906 A1 | 9/2018 | Pivonka et al. | |
| 2019/0030339 A1 | 1/2019 | Baru et al. | |
| 2019/0186702 A1 | 6/2019 | Masson | |

OTHER PUBLICATIONS

Ramon et al., "Changes in scalp potentials and spatial smoothing effects of inclusion of dura layer in human head models for EEG simulations", Frontiers in Neuroengineering, vol. 7, No. 32, Aug. 5, 2014, pp. 1-8.

* cited by examiner

100

105

120

130A  130B

110

EXTERNAL
PROGRAMMER
150

300

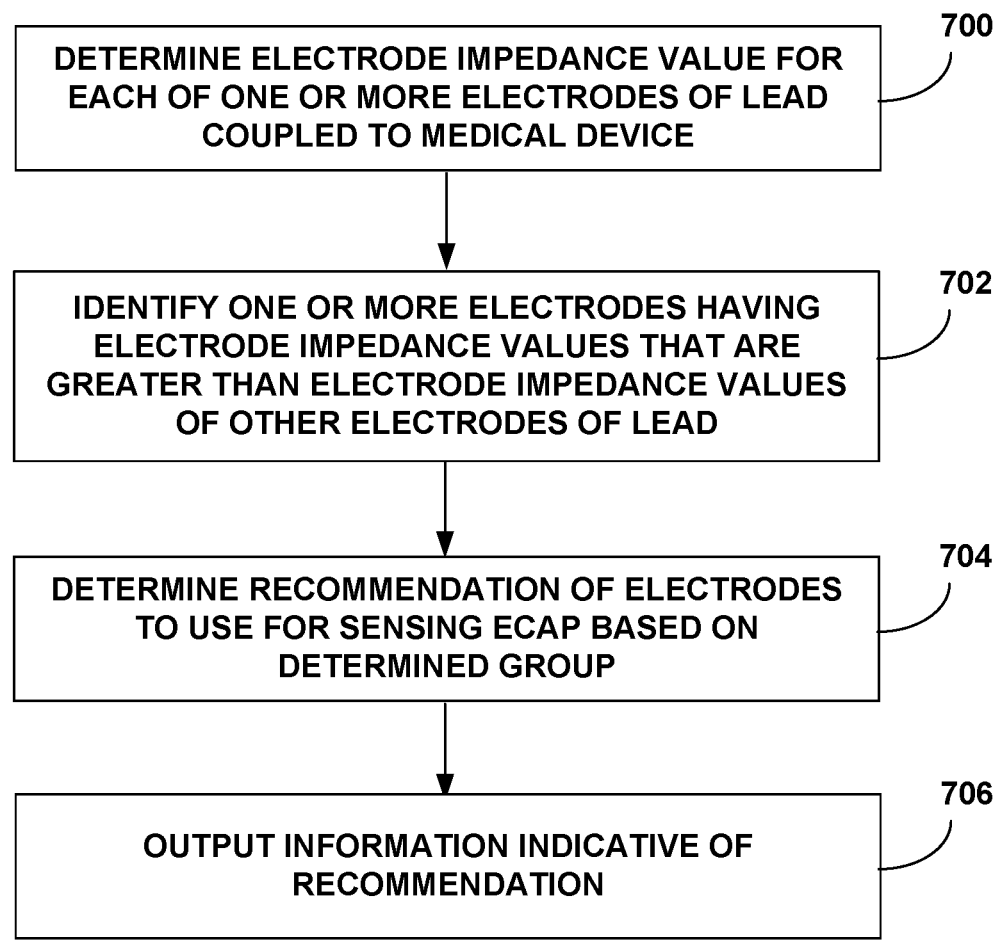

DETERMINE ELECTRODE IMPEDANCE VALUE FOR EACH OF ONE OR MORE ELECTRODES OF LEAD COUPLED TO MEDICAL DEVICE — 700

IDENTIFY ONE OR MORE ELECTRODES HAVING ELECTRODE IMPEDANCE VALUES THAT ARE GREATER THAN ELECTRODE IMPEDANCE VALUES OF OTHER ELECTRODES OF LEAD — 702

DETERMINE RECOMMENDATION OF ELECTRODES TO USE FOR SENSING ECAP BASED ON DETERMINED GROUP — 704

OUTPUT INFORMATION INDICATIVE OF RECOMMENDATION — 706

FIG. 7

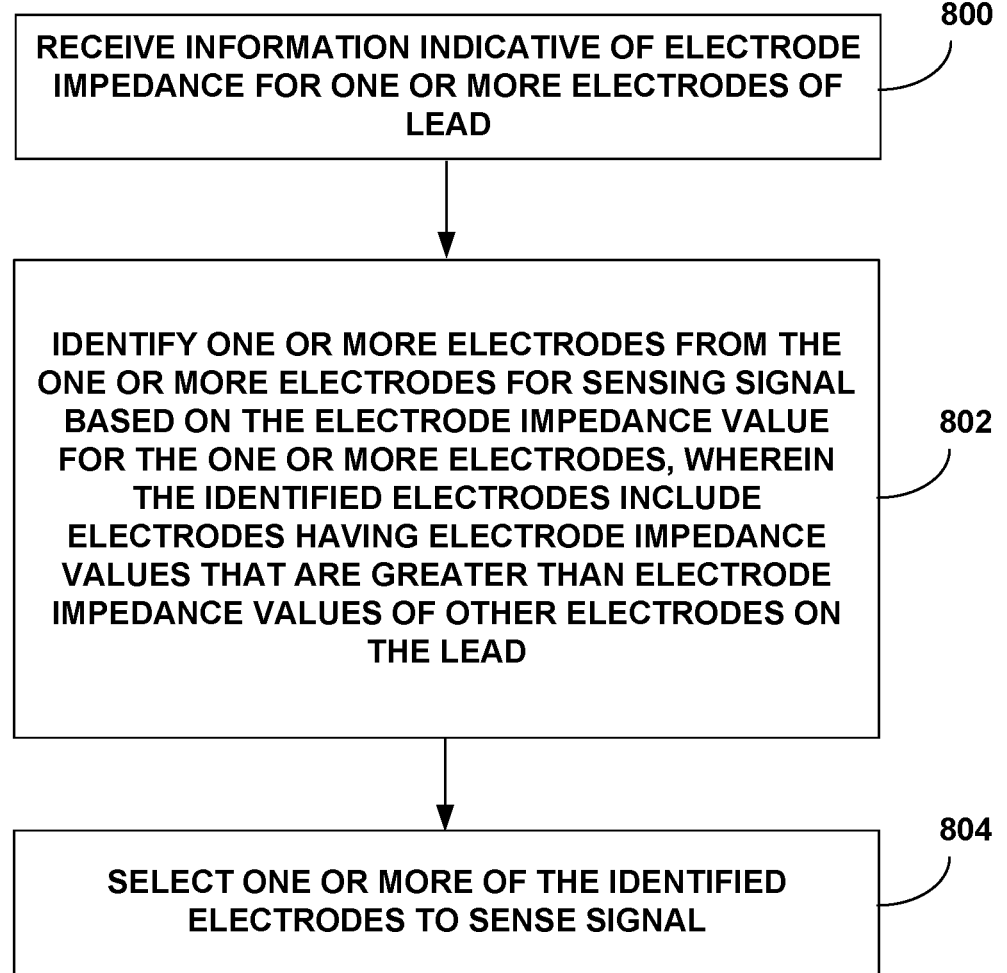

RECEIVE INFORMATION INDICATIVE OF ELECTRODE IMPEDANCE FOR ONE OR MORE ELECTRODES OF LEAD — 800

IDENTIFY ONE OR MORE ELECTRODES FROM THE ONE OR MORE ELECTRODES FOR SENSING SIGNAL BASED ON THE ELECTRODE IMPEDANCE VALUE FOR THE ONE OR MORE ELECTRODES, WHEREIN THE IDENTIFIED ELECTRODES INCLUDE ELECTRODES HAVING ELECTRODE IMPEDANCE VALUES THAT ARE GREATER THAN ELECTRODE IMPEDANCE VALUES OF OTHER ELECTRODES ON THE LEAD — 802

SELECT ONE OR MORE OF THE IDENTIFIED ELECTRODES TO SENSE SIGNAL — 804

FIG. 8

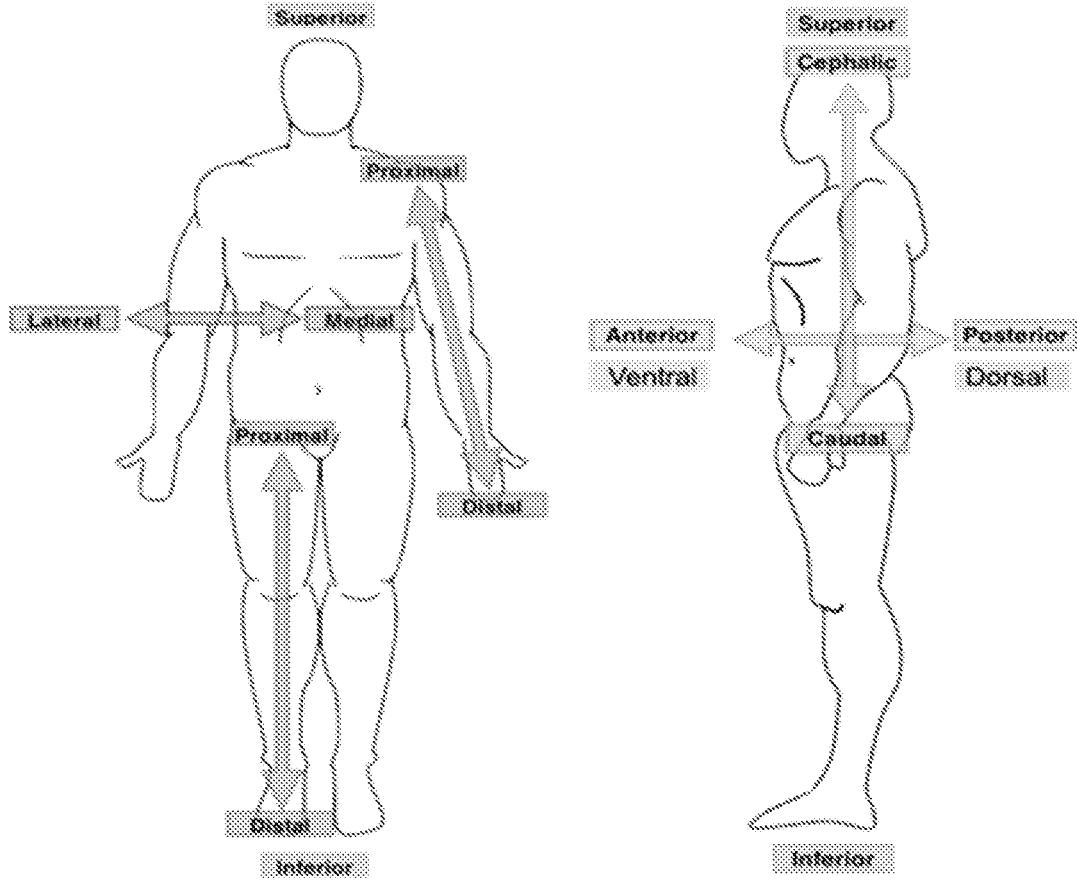
FIG. 9A                    FIG. 9B

ELECTRODE SELECTION BASED ON IMPEDANCE FOR SENSING OR STIMULATION

This application is a U.S. National Stage entry under 35 U.S.C. § 371 of International Application No. PCT/US2022/070735, filed Feb. 18, 2022, which claims priority to U.S. Provisional Patent Application No. 63/152,915, filed Feb. 24, 2021, the entire content of each of which is incorporated herein by reference.

TECHNICAL FIELD

This disclosure generally relates to medical devices, and more specifically, for electrode selection for sensing or stimulation.

BACKGROUND

Medical devices may be external or implanted and may be used to deliver electrical stimulation therapy to patients via various tissue sites to treat a variety of symptoms or conditions such as chronic pain, tremor, Parkinson's disease, epilepsy, urinary or fecal incontinence, sexual dysfunction, obesity, or gastroparesis. A medical device may deliver electrical stimulation therapy via one or more leads that include electrodes located proximate to target locations associated with the brain, the spinal cord, pelvic nerves, peripheral nerves, or the gastrointestinal tract of a patient. Stimulation proximate the spinal cord, proximate the sacral nerve, within the brain, and proximate peripheral nerves are often referred to as spinal cord stimulation (SCS), sacral neuromodulation (SNM), deep brain stimulation (DBS), and peripheral nerve stimulation (PNS), respectively. Electrical stimulation may be delivered to a patient by the medical device in a train of electrical pulses, and parameters of the electrical pulses may include a frequency, an amplitude, a pulse width, and a pulse shape. An evoked compound action potential (ECAP) is synchronous firing of a population of neurons which occurs in response to the application of a stimulus including, in some cases, an electrical stimulation by a medical device.

SUMMARY

In general, systems, devices, and techniques are described for determining electrodes to use for sensing signals and/or outputting stimulation signals. For ease of description and not limitation, the examples are described with respect to sensing evoked compound action potential (ECAP) signals. ECAP signals tend to emanate in all directions from the neural target being sensed in response to an electrical stimulation. This disclosure describes example techniques to determine which electrodes are more likely to reliably sense the ECAP signal. A bone, such as a laminar bone, tends to have higher electrical impedance compared to nearby tissue. Accordingly, the bone tends to restrict the emanation of the ECAP signal and confines the ECAP signal. For instance, a laminar bone tends to constrain the ECAP signal to a region towards the spinal cord. In one or more examples, the electrodes that are under a bone (e.g., ventral to the laminar hone) may be better suited to sense ECAP signals because the bone directs the ECAP signal towards such electrodes. Under the bone refers to the electrodes being fully or partially covered by the hone where the electrode lies on the tissue (e.g., the dura overlaying the spinal cord).

Because the bone tends to have higher electrical impedance, electrodes under the bone tend to have higher electrode impedance as compared to electrodes between bones, or under a lower impedance part of the body such as the ligamentum flavum or the epidural fat. Electrode impedance of an electrode may refer to the impedance between two electrodes on a lead (e.g., bipolar impedance between two electrodes on one lead or between two electrodes on different leads) or impedance between an electrode on a lead and an indifferent electrode (e.g., unipolar impedance), where the indifferent electrode is not on the lead. This disclosure describes example techniques to determine impedance of electrodes from which electrodes that are likely to be under the bone can be selected for sensing ECAP signals.

In this way, rather than relying only on imaging techniques to determine whether electrodes are under bone, the example techniques provide for utilizing electrical measurements, such as impedance obtained at least in part using one or more implanted electrodes, to determine whether electrodes are under the hone, allowing for a less intrusive way of determining electrode positioning for selecting electrodes that are well positioned for ECAP signal sensing. Furthermore, in some examples, having electrodes positioned under the bone may be beneficial because the bone applies pressure to the lead that causes the electrodes to be in closer proximity to the neural target being sensed. Also, although the above is described for selection of implanted electrodes for sensing of ECAP signals, impedance measurements may also be utilized for sensing other types of signals and/or determining which implanted electrodes to use for delivery of stimulation.

In one example, this disclosure describes a medical device comprising processing circuitry configured to determine an electrode impedance value for each of one or more electrodes of a lead coupled to the medical device, identify one or more of the electrodes having electrode impedance values that are greater than electrode impedance values of other electrodes of the lead, from the identified one or more electrodes, determine a recommendation of electrodes to use for sensing a signal, and output information indicative of the recommendation.

In another example, this disclosure describes a method for selecting sensing electrodes that includes receiving information indicative of an electrode impedance value for one or more electrodes of a lead, identifying one or more electrodes from the one or more electrodes for sensing a signal based on the electrode impedance value for the one or more electrodes, wherein the identified electrodes include electrodes having electrode impedance values that are greater than electrode impedance values of other electrodes on the lead, and selecting one or more of the identified electrodes to sense the signal.

In another example, this disclosure describes a method that includes determining an electrode impedance value for each of one or more electrodes of a lead coupled to the medical device, identifying one or more of the electrodes having electrode impedance values that are greater than electrode impedance values of other electrodes of the lead, from the identified one or more electrodes, determining a recommendation of electrodes to use for sensing a signal, and outputting information indicative of the recommendation.

The summary is intended to provide an overview of the subject matter described in this disclosure, it is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

BRIEF DESCRIPTION OF DRAWINGS

FIG. 7 is a flowchart of an example method for electrode selection, in accordance with one or more techniques of this disclosure.

FIG. 8 is a flowchart of another example method for electrode selection, in accordance with one or more techniques of this disclosure.

FIGS. 9A and 9B are conceptual diagrams illustrating anatomical directionality.

DETAILED DESCRIPTION

Figure 1:
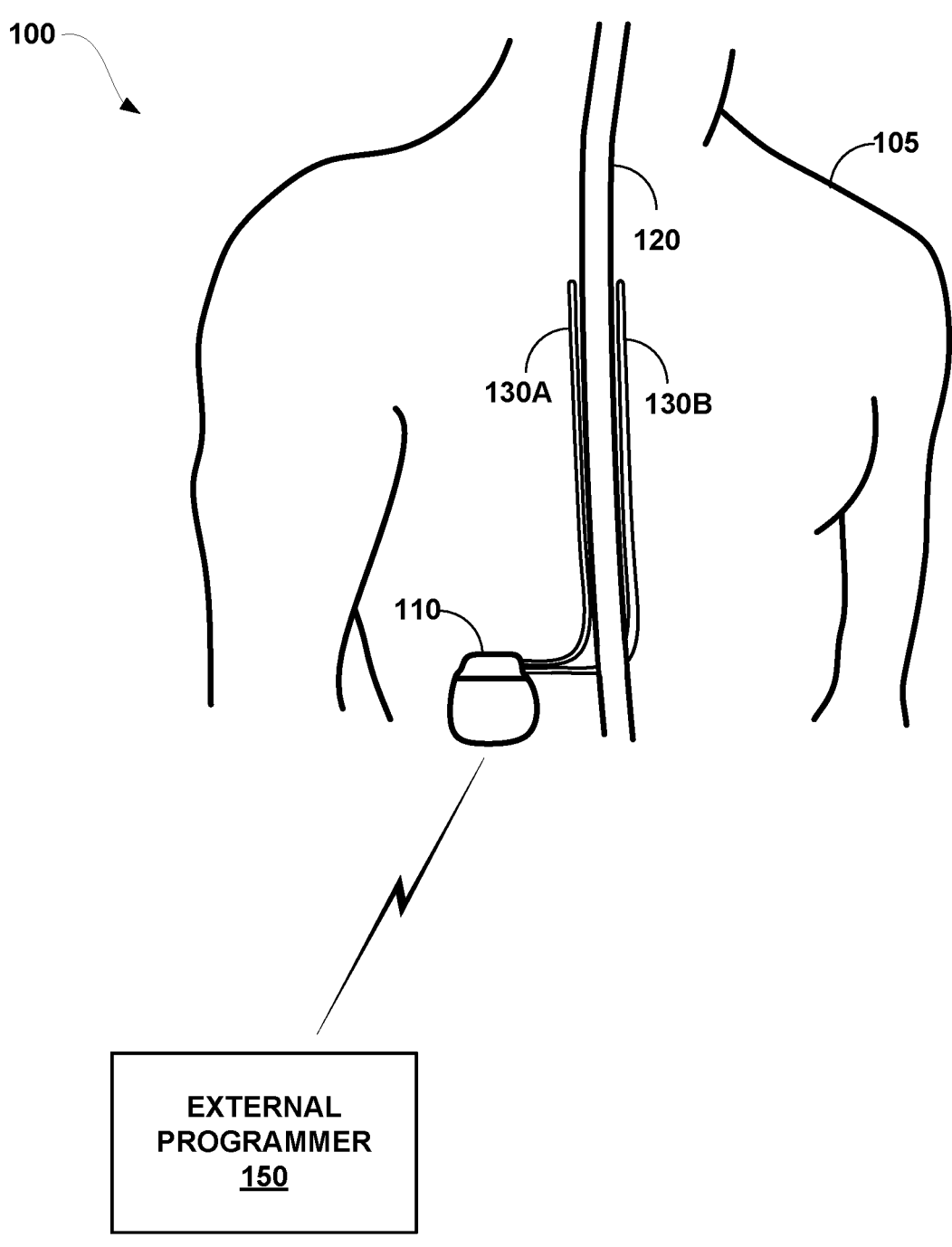
FIG. 1 is a conceptual diagram illustrating an example system that includes an implantable medical device (IMD) configured to deliver spinal cord stimulation (SCS) therapy and an external programmer, in accordance with one or more techniques of this disclosure.

The disclosure describes examples of medical devices, systems, and techniques for determining electrodes to use for sensing signals and/or for outputting stimulation signals. For ease of illustration and not limitation, the examples are described with respect to sensing evoked compound action potential (ECAP) signals. ECAP signals are a measure of neural recruitment because each ECAP signal represents the superposition of electrical potentials generated from a population of axons firing in response to an electrical stimulus (e.g., a stimulation pulse). The ECAP signal may be detectable as being a separate event from the stimulation itself, and the ECAP signal may reveal characteristics of the effect of the stimulation on the nerve fibers. That is, changes in a characteristic (e.g., an amplitude of a portion of the signal or area under the curve of the signal) of an ECAP signal occur as a function of how many axons have been activated by the delivered stimulation pulse. For a given set of parameter values that define the stimulation pulse and a given distance between the electrodes and target nerve, the detected ECAP signal may have a certain characteristic value (e.g., amplitude). Because ECAP signals reveal characteristics of the effect of the stimulation on the nerve fibers, a medical device may utilize the ECAP signals to control the stimulation pulse (e.g., amplitude, pulse width, frequency, etc.) to provide efficacious therapy.

However, ECAP signals tend to emanate in all directions and have a relatively low duration. Accordingly, an electrode that is used for sensing the ECAP signal may sense only a small portion of the ECAP signal. Therefore, the amplitude of the ECAP signal that the electrode relays to a sensing circuit may be relatively low. In some cases, it may be difficult for the sensing circuit to distinguish between the ECAP signal and noise due to the relatively low amplitude of the ECAP signal received from the electrode.

This disclosure describes example techniques for selecting electrodes for sensing ECAP signals, where the selected electrodes are positioned in locations where the ECAP signals are confined. In this way, the amplitude of the ECAP signals that the electrodes sense may be relatively high, allowing the sensing circuit to differentiate between the ECAP signal and noise. Moreover, this disclosure describes example techniques for positioning the electrodes during lead implantation such that electrodes that are to be used for sensing ECAP signals are positioned in locations where the ECAP signals are confined.

In one or more examples, bone within the patient may function as a high impedance shield that constrains the ECAP signal (e.g., constrains the propagation of the ECAP signal). An electrode that is under the bone may therefore sense a higher amplitude ECAP signal as compared to an electrode located in between bones. For ease of illustration and as example, this disclosure describes the examples with respect to a laminar bone for spinal cord stimulation and sensing. However, the techniques are not limited to a laminar bone.

An electrode under the bone may mean that if the patient is lying prone, the electrode is located in the dorsal epidural space of the spine, and the laminar bone is dorsal to the electrode and partially or fully covering the electrode. An electrode between bones may mean that if the patient is lying prone, the electrode is again located in the dorsal epidural space of the spinal cord, and there is no laminar bone that is fully covering the electrode. For instance, under the bone may mean that the spinal cord and the laminar bone "sandwich" the electrode.

The laminar bone tends to have higher resistivity (e.g., 16 kOhms-cm) relative to epidural fat (e.g., 2.5 kOhm-cm) or dura e.g., 1.67 kOhm-cm). As such, an ECAP signal, sensed by an electrode under the laminar bone, is more strongly directed towards the spinal cord than an ECAP signal sensed by an electrode in an intralaminar space. For instance, the laminar bone acts as a high impedance shield that keeps the ECAP signal constrained towards the spinal cord. Accordingly, there may be benefit in utilizing the electrode under the laminar bone for sensing ECAP signals.

In some cases, there may be benefits in utilizing an electrode that is under the laminar bone for stimulation. There may be a plurality of laminar bones along the spinal cord, and electrodes under a first laminar bone may be useful for sensing, and electrodes under a second laminar bone may be useful for stimulation. For instance, because the laminar bone functions as a high impedance shield, stimulation that is output by a cylindrical electrode under the laminar bone is directed towards the spinal cord and less of the stimulation is lost to other tissue as compared to stimulation that is output by an electrode in the intralaminar space, Because the stimulation from an electrode under the laminar bone is better directed towards the spinal cord, the stimulation threshold may be lower. That is, the amount of stimulation needed to provide effective therapy may be lower, as compared to examples where the electrode is in the intralaminar space, because the stimulation from an electrode under the laminar bone is directed back to the spinal cord (e.g., the spinal cord receives a larger percentage of the stimulation field).

Lower stimulation threshold, also called neural activation threshold, may be beneficial for reduced energy consumption, longer battery life, and less stimulation artifact. In some cases, the stimulation artifact is dependent on the stimulation amplitude (e.g., linearly dependent on the amount of stimulation), and the amount of stimulation artifact may impact the ability of the sensing circuit to resolve ECAP signals (e.g., differentiate between ECAP signals and stimulation artifacts).

Accordingly, having sensing electrodes and/or stimulation electrodes under the laminar bone may provide benefits for sensing signals (e.g., ECAP signals) and/or outputting stimulation signals. In addition, the laminar bone may provide a mass effect that exerts on the lead (e.g., the rigid laminar bone pushes the electrode under the laminar bone closer to the spinal cord). By pushing the electrode under the laminar bone closer to the spinal cord, the electrode may sense higher amplitudes for the ECAP signals, as well as direct more of the stimulation to the spinal cord.

However, determining whether an electrode is under a bone may be difficult, especially post-operative in the patient's home or in a clinician's office. Even with relatively inexpensive imaging techniques such as fluorographic imaging, it may be difficult to view the laminar bone and lead.

This disclosure describes example techniques to determine which electrodes may be well suited for sensing signals (e.g., ECAP signals but any other types of signals are possible) and/or for outputting stimulation signals. As described above, a bone (e.g., laminar bone) tends to be relatively high impedance compared to nearby tissue. Accordingly, the impedance of electrodes under the laminar bone tends to be higher compared to electrodes in the intralaminar space (e.g., between two laminar bones). Electrode impedance value of an electrode may refer to the impedance value between two electrodes on a lead (e.g., bipolar impedance between two electrodes on same lead or between two electrodes on different leads) or impedance value between an electrode on a lead and an indifferent electrode (e.g., unipolar impedance), where the indifferent electrode is not on the lead and may be, for example, on an implantable stimulator housing.

For example, the medical device may output current having a certain amplitude through a first electrode, and the current may return back to the medical device through a second electrode. The medical device may determine voltage difference between the first and second electrodes, and determine the electrode impedance value based on the current amplitude and voltage difference. For electrodes under the laminar bone, the electrical path for the current may be through the more highly resistive laminar bone, and therefore, the electrode impedance value of the electrodes under the laminar bone may be higher than the electrode impedance value of electrodes in the intralaminar space.

In one or more examples, processing circuitry of a medical device may determine the electrode impedance value of electrodes on a lead. The processing circuitry may identify one or more electrodes of the lead having electrode impedance values that are greater than electrode impedance value of other electrodes on the lead. The identified one or more electrodes may be a group of one or more electrodes. The electrodes in the group of electrodes may be likely to be under bone (e.g., wider laminar bone) because the electrode impedance value of the electrodes in the group of electrodes is higher than the electrode impedance value of the other electrodes. In some examples, the processing circuitry may identify the group of electrodes based on all electrodes in the group having an impedance greater than or equal to a threshold impedance. In some examples, the processing circuitry may identify the group of electrodes based on relative impedances of the electrodes (e.g., the group may include electrodes having higher impedance relative to other electrodes).

In this way, based on electrode impedance value, it may be possible to determine which electrodes are under bone. In some examples, the processing circuitry determines a recommendation of electrodes to use for sensing and/or stimulation based on the determined group, and output information indicative of the recommendation. In some examples, the processing circuitry may output the electrode impedance value for one or more of the electrodes, and a clinician may select electrodes for stimulation and/or sensing based on the electrode impedance value for the one or more electrodes.

FIG. 1 is a conceptual diagram illustrating an example system 100 that includes an implantable medical device (IMD) 110 configured to deliver spinal cord stimulation (SCS) therapy and an external programmer 150, in accordance with one or more techniques of this disclosure. Although the techniques described in this disclosure are generally applicable to a variety of medical devices including external devices and IMDs, application of such techniques to IMDs and, more particularly, implantable electrical stimulators (e.g., neurostimulators) will be described for purposes of illustration. More particularly, the disclosure will refer to an implantable SCS system for purposes of illustration, but without limitation as to other types of medical devices or other therapeutic applications of medical devices.

As shown in the example of FIG. 1, system 100 includes an IMD 110, leads 130A and 130B, and external programmer 150 shown in conjunction with a patient 105, who is ordinarily a human patient. In the example of FIG. 1, IMD 110 is an implantable electrical stimulator that is configured to generate and deliver electrical stimulation therapy to patient 105 via one or more electrodes of leads 130A and/or 130B (collectively, "leads 130"), e.g., for relief of chronic pain or other symptoms. In other examples, IMD 110 may be coupled to a single lead carrying multiple electrodes or more than two leads each carrying multiple electrodes. IMD 110 may be a chronic electrical stimulator that remains implanted within patient 105 for weeks, months, or even years. In other examples, IMD 110 may be a temporary, or trial, stimulator used to screen or evaluate the efficacy of electrical stimulation for chronic therapy. In one example, IMD 110 is implanted within patient 105, while in another example, IMD 110 is an external device coupled to percutaneously implanted leads. In some examples, IMD 110 uses one or more leads, while in other examples, IMD 110 is leadless.

IMD 110 may be constructed of any polymer, metal, or composite material sufficient to house the components of IMD 110 (e.g., components illustrated in FIG. 2) within patient 105. In this example, IMD 110 may be constructed with a biocompatible housing, such as titanium or stainless steel, or a polymeric material such as silicone, polyurethane, or a liquid crystal polymer, and surgically implanted at a site in patient 105 near the pelvis, abdomen, or buttocks. In other examples, IMD 110 may be implanted within other suitable sites within patient 105, which may depend, for example, on the target site within patient 105 for the delivery of electrical stimulation therapy. The outer housing of IMD 110 may be configured to provide a hermetic seal for components, such as a rechargeable or non-rechargeable power source and stimulation and sensing circuitry. In addition, in some examples, the outer housing of IMD 110 is selected from a material that facilitates receiving energy to charge the rechargeable power source.

Electrical stimulation energy, which may be constant current or constant voltage-based pulses, for example, is delivered from IMD 110 to one or more target tissue sites of patient 105 via one or more electrodes (not shown) of implantable leads 130. In the example of FIG. 1, leads 130 carry electrodes that are placed adjacent to the target tissue of spinal cord 120. One or more of the electrodes may be disposed at a distal tip of a lead 130 and/or at other positions at intermediate points along the lead. Leads 130 may be implanted and coupled to IMD 110. The electrodes may transfer electrical stimulation generated by an electrical stimulation generator in MID 110 to tissue of patient 105. Although leads 130 may each be a single lead, lead 130 may include a lead extension or other segments that may aid in implantation or positioning of lead 130. In some other examples, IMD 110 may be a leadless stimulator with one or more arrays of electrodes arranged on a housing of the stimulator rather than leads that extend from the housing. In addition, in some other examples, system 100 may include one lead or more than two leads, each coupled to IMD 110 and directed to similar or different target tissue sites.

The electrodes of leads 130 may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), any combination thereof (e.g., ring electrodes and segmented electrodes) or any other type of electrodes capable of forming unipolar, bipolar or multipolar electrode combinations for therapy. Ring electrodes arranged at different axial positions at the distal ends of lead 130 will be described for purposes of illustration.

The deployment of electrodes via leads 130 is described for purposes of illustration, but arrays of electrodes may be deployed in different ways. For example, a housing associated with a leadless stimulator may carry arrays of electrodes, e.g., rows anchor columns (or other patterns). Such electrodes may be arranged as surface electrodes, ring electrodes, or protrusions. As a further alternative, electrode arrays may be formed by rows and/or columns of electrodes on one or more paddle leads. In some examples, electrode arrays include electrode segments, which are arranged at respective positions around a periphery of a lead, e.g., arranged in the form of one or more segmented rings around a circumference of a cylindrical lead. In other examples, one or more of leads 130 are linear leads having 8 ring electrodes along the axial length of the lead or 16 ring electrodes along the axial length. In another example, the electrodes are segmented rings arranged in a linear fashion along the axial length of the lead and at the periphery of the lead.

The stimulation parameter set of a therapy stimulation program that defines the stimulation pulses of electrical stimulation therapy by IMD 110 through the electrodes of leads 130 may include information identifying which electrodes have been selected for delivery of stimulation according to a stimulation program, the polarities of the selected electrodes, i.e., the electrode combination for the program, voltage or current amplitude, pulse frequency, pulse width, and/or pulse shape of stimulation delivered by the electrodes. These stimulation parameters values that make up the stimulation parameter set that defines pulses may be predetermined parameter values defined by a user and/or automatically determined by system 100 based on one or more factors or user input.

In some examples, IMD 110 may deliver stimulation pulses that contribute to therapy perceived by patient 105. IMD 110 may also sense signals. In some examples, IMD 110 may detect ECAP signals elicited by stimulation pulses. In some examples, stimulation pulses configured to provide therapy may prevent IMD 110 from detecting ECAP signals (e.g., because the pulse width of the stimulation pulses are long enough to interfere with propagating ECAP signals), Therefore, if control pulses (e.g., pulses that may or may not contribute to therapy) separate from informed pulses configured to provide therapy are needed to elicit a detectable ECAP signal, system 100 may employ an ECAP test stimulation program that defines stimulation parameter values that define control pulses delivered by IMD 110 through at least some of the electrodes of leads 130, These stimulation parameter values may include information identifying which electrodes have been selected for delivery of control pulses, the polarities of the selected electrodes, i.e., the electrode combination for the program, and voltage or current amplitude, pulse frequency, pulse width, and pulse shape of stimulation delivered by the electrodes.

The stimulation signals (e.g., one or more stimulation pulses or a continuous stimulation waveform) defined by the parameters of each ECAP test stimulation program are configured to evoke a compound action potential from nerves. In some examples, the ECAP test stimulation program defines when the control pulses are to be delivered to the patient based on the frequency and/or pulse width of the informed pulses. The stimulation defined by each ECAP test stimulation program may not be intended to provide or contribute to therapy for the patient, but the patient may perceive the control pulses in some examples.

The use of ECAP test stimulation program is one example and should not be considered limiting. The example techniques described in this disclosure may be applicable generally to sensing electrical signals, with one example including ECAP signals generated in response to informed pulses used for delivery stimulation therapy or generated in response to ECAP test stimulation program. Also, although the example techniques are described with respect to ECAP signals, the techniques described in this disclosure may be applicable to sensing signals more generally with ECAP signals being one example of signals that are sensed.

Although FIG. 1 is directed to SCS therapy, e.g., used to treat pain, in other examples system 100 may be configured to treat any other condition that may benefit from electrical stimulation therapy. For example, system 100 may be used to treat tremor, Parkinson's disease, epilepsy, a pelvic floor disorder (e.g., urinary incontinence or other bladder dysfunction, fecal incontinence, pelvic pain, bowel dysfunction, or sexual dysfunction), obesity, gastroparesis, or psychiatric disorders (e.g., depression, mania, obsessive compulsive disorder, anxiety disorders, and the like). In this manner, system 100 may be configured to provide therapy taking the form of deep brain stimulation (DBS), peripheral nerve stimulation (PNS), peripheral nerve field stimulation (PNFS), cortical stimulation (CS), pelvic floor stimulation, gastrointestinal stimulation, or any other stimulation therapy capable of treating a condition of patient 105.

In some examples, lead 130 includes one or more sensors configured to allow IMD 110 to monitor one or more parameters of patient 105, such as patient activity, pressure, temperature, or other characteristics. The one or more sensors may be provided in addition to, or in place of, therapy delivery by lead 130.

IMD 110 is configured to deliver electrical stimulation therapy to patient 105 via selected combinations of electrodes carried by one or both of leads 130, alone or in combination with an electrode carried by or defined by an outer housing of IMD 110. The target tissue for the electrical stimulation therapy may be any tissue affected by electrical stimulation, which may be in the form of electrical stimulation pulses or continuous waveforms. In some examples, the target tissue includes nerves, smooth muscle, or skeletal muscle. In the example illustrated by FIG. 1, the target tissue is tissue proximate spinal cord 120, such as within an intrathecal space or epidural space of spinal cord 120, or, in some examples, adjacent nerves that branch off spinal cord 120. Leads 130 may be introduced adjacent to spinal cord 120 in via any suitable region, such as the thoracic, cervical, or lumbar regions. Stimulation of spinal cord 120 may, for example, prevent pain signals from traveling through spinal cord 120 and to the brain of patient 105. Patient 105 may perceive the interruption of pain signals as a reduction in pain and, therefore, efficacious therapy results. In other examples, stimulation of spinal cord 120 may produce paresthesia which causes a tingling sensation that may reduce the perception of pain by patient 105 and thus, provide efficacious therapy results.

IMD 110 is configured to generate and deliver electrical stimulation therapy to a target stimulation site within patient 105 via the electrodes of leads 130 to patient 105 according to one or more therapy stimulation programs. A therapy stimulation program defines values for one or more parameters (e.g., a parameter set) that define an aspect of the therapy delivered by IMD 110 according to that program. For example, a therapy stimulation program that controls delivery of stimulation by IMD 110 in the form of pulses may define values for voltage or current pulse amplitude, pulse width, pulse rate (e.g., pulse frequency), electrode combination, pulse shape, etc. for stimulation pulses delivered by IMD 110 according to that program.

Furthermore, IMD 110 may be configured to deliver control stimulation to patient 105 via a combination of electrodes of leads 130, alone or in combination with an electrode carried by or defined by an outer housing of IMD 110 in order to detect ECAP signals (e.g., control pulses and/or informed pulses). The tissue targeted by the stimulation may be the same or similar tissue targeted by the electrical stimulation therapy, but IMD 110 may deliver stimulation pulses for ECAP signal detection via the same, at least some of the same, or different electrodes. Since control stimulation pulses can be delivered in an interleaved manner with informed pulses (e.g., when the pulses configured to contribute to therapy interfere with the detection of ECAP signals or pulse sweeps intended to detect migration of leads 130 via ECAP signals do not correspond to pulses intended for therapy purposes), a clinician and/or user may select any desired electrode combination for informed pulses.

In some examples, to minimize the impact of stimulation artifacts, the sensing electrodes and stimulation electrodes may be spaced a relatively high distance. For instance, if the electrodes used for stimulation are on the distal end of one of leads 130 (e.g., furthest away from IMD 110), then the electrodes used for sensing may be on a proximal end of one of leads 130 (e.g., closest to IMD 110), or vice-versa. Having the stimulation and sensing electrodes spaced a relatively high distance is one example and should not be considered limiting.

Like the electrical stimulation therapy, the control stimulation may be in the form of electrical stimulation pulses or continuous waveforms. In one example, each control stimulation pulse may include a balanced, biphasic square pulse that employs an active recharge phase. However, in other examples, the control stimulation pulses may include a monophasic pulse followed by a passive recharge phase. In other examples, a control pulse may include an imbalanced biphasic portion and a passive recharge portion. Although not necessary, a bi-phasic control pulse may include an interphase interval between the positive and negative phase to promote propagation of the nerve impulse in response to the first phase of the bi-phasic pulse. The control stimulation may be delivered without interrupting the delivery of the electrical stimulation informed pulses, such as during the window between consecutive informed pulses. The control pulses may elicit an ECAP signal from the tissue, and IMD 110 may sense the ECAP signal via two or more electrodes on leads 130. In cases where the control stimulation pulses are applied to spinal cord 120, the signal may be sensed by IMD 110 from spinal cord 120.

IMD 110 can deliver control stimulation to a target stimulation site within patient 105 via the electrodes of leads 130 according to one or more ECAP test stimulation programs. The one or more ECAP test stimulation programs may be stored in a storage device of IMD 110. Each ECAP test program of the one or more ECAP test stimulation programs includes values for one or more parameters that define an aspect of the control stimulation delivered by IMD 110 according to that program, such as current or voltage amplitude, pulse width, pulse frequency, electrode combination, and, in some examples timing based on informed pulses to be delivered to patient 105.

A user, such as a clinician or patient 105, may interact with a user interface of an external programmer 150 to program IMD 110. Programming of IMO 110 may refer generally to the generation and transfer of commands, programs, or other information to control the operation of IMD 110. In this manner, IMD 110 may receive the transferred commands and programs from external programmer 150 to control stimulation. Example of the stimulation includes electrical stimulation therapy (e.g., informed pulses) and/or control stimulation (e.g., control pulses). For example, external programmer 150 may transmit therapy stimulation programs, ECAP test stimulation programs, stimulation parameter adjustments, therapy stimulation program selections, ECAP test program selections, user input, or other information to control the operation of IMD 110, e.g., by wireless telemetry or wired connection.

In some cases, external programmer 150 may be characterized as a physician or clinician programmer if it is primarily intended for use by a physician or clinician. In other cases, external programmer 150 may be characterized as a patient programmer if it is primarily intended for use by a patient. A patient programmer may be generally accessible to patient 105 and, in many cases, may be a portable device that may accompany patient 105 throughout the patient's daily routine. For example, a patient programmer may receive input from patient 105 when the patient wishes to terminate or change electrical stimulation therapy, or when a patient perceives stimulation being delivered. In general, a physician or clinician programmer may support selection and generation of programs by a clinician for use by IMD 110, whereas a patient programmer may support adjustment and selection of such programs by a patient during ordinary use. In other examples, external programmer 150 may include, or be part of, an external charging device that recharges a power source of IMD 110, In this manner, a user may program and charge MD 110 using one device, or multiple devices.

As described herein, information may be transmitted between external programmer 150 and MD 110. Therefore, IMD 110 and external programmer 150 may communicate via wireless communication using any techniques known in the art. Examples of communication techniques may include, for example, radiofrequency (RF) telemetry and inductive coupling, but other techniques are also contemplated. In some examples, external programmer 150 includes a communication head that may be placed proximate to the patient's body near the IMD 110 implant site to improve the quality or security of communication between IMD 110 and external programmer 150. Communication between external programmer 150 and IMD 110 may occur during power transmission or separate from power transmission.

In some examples, IMD 110, in response to commands from external programmer 150, delivers electrical stimulation therapy according to a plurality of therapy stimulation programs to a target tissue site of the spinal cord 120 of patient 105 via electrodes (not depicted) on leads 130. In some examples, IMD 110 modifies therapy stimulation programs as therapy needs of patient 105 evolve over time. For example, the modification of the therapy stimulation programs may cause the adjustment of at least one parameter of the plurality of informed pulses. When patient 105 receives the same therapy for an extended period, the efficacy of the therapy may be reduced. In some cases, parameters of the plurality of informed pulses may be automatically updated.

As described above, BID 110 may be configured to sense signals using one or more electrodes of leads 130 and output stimulation using one or more electrodes of leads 130. In some examples, the exact placement of SCS (spinal cord simulation) leads 130 in or adjacent to spinal cord 120 can influence the thresholds for neural activation (e.g., amount of stimulation needed to provide efficacious therapy), the stimulation artifacts generated from the stimulation, and the ability to resolve ECAP signals from spinal cord 120 (e.g., ability to differentiate between ECAP signals and noise and/or artifacts), in some examples, the factors that influence neural activation threshold, stimulation artifacts, and ability to resolve ECAP signals, among others, include how medial/lateral lead 130 are placed on spinal cord 120, the thickness of the cerebrospinal fluid between the electrodes and spinal cord 120, and the location of the electrodes relative to the laminar bone.

The laminar bone may affect stimulation threshold and the ability to sense ECAPs in several different ways. As one example, the bone has a much higher resistivity (16 kOhm-cm) relative to epidural fat (2.5 kOhm-cm) or dura (1.67 kOhm-cm). Accordingly, the stimulation field generated from, or the ECAP signal sensed by, an electrode under the laminar bone is more strongly directed towards spinal cord 120 than that from an electrode in the intralaminar space. For instance, the bone acts as a high impedance shield that keeps the field (e.g., stimulation field or ECAP signal) constrained towards spinal cord 120.

For instance, an ECAP signal that originates from under the laminar bone may be constrained by the laminar bone. Therefore, an electrode under the laminar bone is likely to sense more of the field from the ECAP signal as compared to an electrode in an intralaminar space, and the amplitude of ECAP signal will be greater from the electrode under the laminar bone. Similarly, a stimulation signal that an electrode under the laminar bone outputs may be constrained by the laminar bone, and therefore, the stimulation signal will be more directed toward spinal cord 120. Accordingly, there may be efficiency gain in the stimulation signal as a lesser amount of stimulation signal (e.g., amplitude) may be needed to produce efficacious therapy because more of the stimulation signal is directed to spinal cord 120. For instance, there may be a plurality of laminar bones along spinal cord 120, and electrodes under a first laminar bone may be used for sensing, and electrodes under a second laminar bone may be used for stimulation.

In some examples, the laminar bone may have a mass effect that the laminar bone exerts on leads 130. The rigid bone physically pushes the electrode under the bone closer to spinal cord 120. This serves to lower neural activation thresholds and increase ECAP amplitudes, versus an equivalent electrode in the intralaminar space. Lower neural activation thresholds are also desired because they result in lower energy consumption, longer battery life and less stimulation artifact. In some cases, stimulation artifact is generally linearly dependent on stimulation amplitude, and the amount of stimulation artifact affects the capability of IMD 110 to resolve ECAPs (e.g., differentiate between ECAP signals and artifacts).

The therapeutic needs of patient 105 may determine which electrodes to use for stimulation. For instance, in some cases, selecting electrodes exclusively under the laminar bone may not always the optimal choice. The stimulation resulting from an electrode under the bone may be perceived by patient 105 as too focal and "intense," The clinician may be willing to accept higher stimulation amplitudes (with the associated higher current consumption from the battery) so as to provide stimulation coverage that is better tolerated by the subject. In some examples, the clinician may start with providing stimulation using an electrode under the laminar bone, and only if patient 105 experiences discomfort would the clinician select a different electrode.

However, for sensing signals, such as ECAP signals, there may be no impact to patient 105. That is, patient 105 may not perceive any sensing of signals, and therefore, any electrode available for sensing may be suitable from the perspective of patient 105.

During surgery, it may be difficult for the surgeon to view and confirm that one or more electrodes of leads 130 are under the laminar bone. For instance, the surgeon may not be able to identify the laminar bone with fluorography. Also, after surgery, there is a possibility that leads 130 migrated. Accordingly, even if the surgeon were able to confirm that one or more of the electrodes of leads 130 are under the laminar bone, it is possible that leads 130 have moved after surgery, and the electrodes that were originally under the laminar bone are no longer under the laminar bone, but other electrodes are now under the laminar bone.

This disclosure describes example techniques to utilize impedance measurements to determine whether an electrode is under a hone (e.g., laminar bone), For instance, as described above, the impedance of the laminar bone is relatively high. Therefore, the electrode impedance value of an electrode under the laminar bone may also be relatively high. The electrode impedance value of an electrode may be unipolar (e.g., between the electrode and an indifferent electrode such as the electrode on the housing of IMD 110) or bipolar (e.g., between two electrodes on leads 130 or between one electrode on lead 130A and another electrode on lead 130B). In both cases, because the laminar bone will be part of the electrical circuit used to determine the electrode impedance value, the impedance of the laminar bone causes the impedance of the electrode to increase.

As one example, IMD 110 may output a current from one electrode with a return path through another electrode. For unipolar, the electrode that outputs the current may be an electrode on one of leads 130, and the return path may be through the indifference electrode. For bipolar, the electrode that outputs the current may be an electrode on one of leads 130, and the return path may be through an electrode on one leads 130 (e.g., same lead or different lead). For unipolar or bipolar electrode impedance value determination, IMD 110 may determine the voltage difference between the two electrodes (e.g., between electrode on lead and indifferent electrode or between the two electrodes on leads), and divide the determined voltage by the current that IMD 110 output to determine the impedance.

IMD 110 may determine an electrode impedance value for one or more electrodes of leads 130 coupled to IMD 110, and identify one or more electrodes of the lead having electrode impedance values that are greater than electrode impedance values of other electrodes on leads 130. The identified one or more electrodes may be a group of one or more electrodes. For instance, IMD 110 may determine which electrodes have relatively high impedance values compared to other electrodes on leads 130.

There may be various example ways in which to identify the one or more electrodes (e.g., group of one or more electrodes). As one example, IMD 110 may select N electrodes having the highest impedance. As another example, IMD 110 may determine a threshold impedance value, and electrodes having the impedance greater than threshold may be in the group, and electrodes having impedance less than threshold are not in the group. The threshold impedance value may be a set value or may be determined based on the impedance values (e.g., the threshold impedance value is average of the electrode impedance values). The above are some example techniques to identify the group of one or more electrodes, and the example techniques should not be considered limited to the above examples.

In some examples, from the group of one or more electrodes, IMD 110 may determine a recommendation of electrodes to use for sensing the ECAP signal. As one example, IMD 110 may select a pair of electrodes from the group of electrodes that are sequential to one another (e.g., there is no electrode between the pair of electrodes). As another example, to reduce artifact, there may be benefit in having the sensing electrodes and stimulation electrodes be separated. Accordingly, MID 110 may select a pair of electrodes from the group of electrodes that are most proximal (closer to IMD 110) or distal (away from IMD 110) on leads 130 for sensing, and use electrodes that are on the opposite end of leads 130 for stimulation.

IMD 110 may output information indicative of the recommendation (e.g., to programmer 150), Programmer 150 may display the recommendation for clinician confirmation and the clinician may configure the sensing circuitry of IMD 110 to receive signals sensed by the recommended electrodes for determining the ECAP Similarly IMD 110 may determine a recommendation of electrodes to use for stimulation based on the electrode impedance value and in some examples based on the amplitude of the ECAP signal), and output the recommendation (e.g., to programmer 150). Programmer 150 may display the recommendation for clinician confirmation and the clinician may configure the stimulation circuitry of IMD 110 to output stimulation signals using the recommended electrodes.

In some examples, rather than providing a recommendation, IMD 110 may output the electrode impedance values for the electrodes. The clinician may then determine which electrodes to use for sensing and stimulation. For example, a manual (or other guide or instructions) for operating IMD

110 and selecting electrodes may instruct a clinician to receive information indicative of an electrode impedance value for one or more electrodes of a lead, and identify one or more electrodes (e.g., a group of one or more electrodes) from the one or more electrodes for sensing a signal (e.g., ECAP signal) based on the electrode impedance value for the one or more electrodes. The identified electrodes (e.g., group of one or more electrodes) may include electrodes having electrode impedance values that are greater than electrode impedance value of other electrodes on the lead. The manual may also instruct the clinician to select one or more electrodes from the identified electrodes to sense the signal. The clinician may then program the sensing circuit of IMD 110 to sense signals from the selected one or more electrodes.

Figure 2:
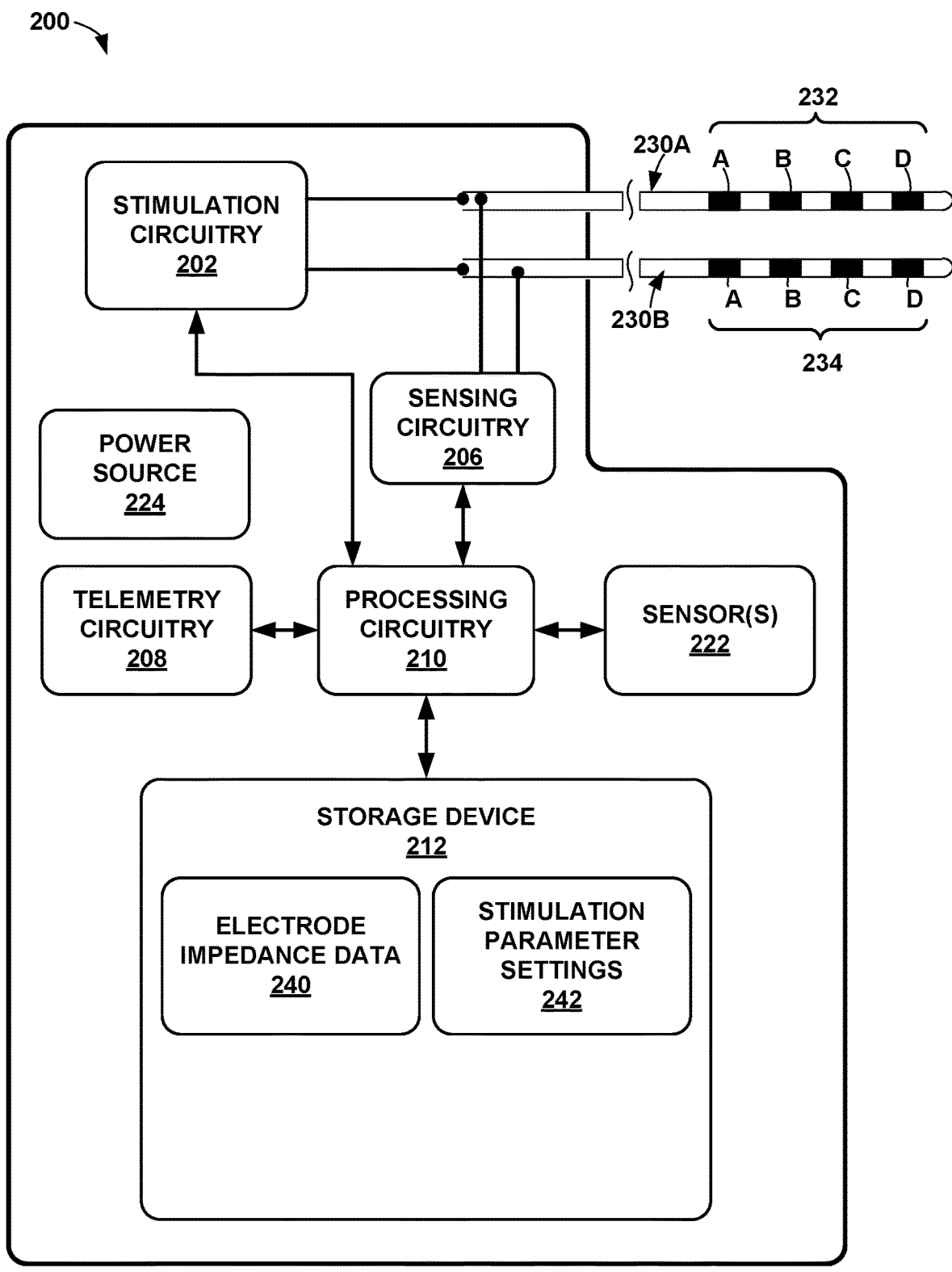
FIG. 2 is a block diagram illustrating an example configuration of components of an implantable medical device (IMD), in accordance with one or more techniques of this disclosure.

FIG. 2 is a block diagram illustrating an example configuration of components of art IMD 200, in accordance with one or more techniques of this disclosure. IMD 200 may be an example of IMD 110 of FIG. 1, in the example shown in FIG. 2, IMD 200 includes stimulation generation circuitry 202, sensing circuitry 206, telemetry circuitry 208, processing circuitry 210, storage device 212, sensor(s) 112, and power source 224.

In the example shown in FIG. 2, storage device 212 stores baseline electrode impedance value data 240 and stimulation parameter settings 242 in separate memories within storage device 212 or separate areas within storage device 212. In some examples, stimulation parameter settings 242 may include stimulation parameter values (sometimes referred to as "sets of therapy parameters") for respective different stimulation programs selectable by the clinician or patient for therapy. In this manner, each stored therapy stimulation program, or set of stimulation parameter values, of stimulation parameter settings 242 defines values for a set of electrical stimulation parameters (e.g., a stimulation parameter set), such as a stimulation electrode combination, electrode polarity, current or voltage amplitude, pulse width, pulse rate, and pulse shape.

Storage device 212 may also store ECAP test stimulation programs, as part of stimulation parameter settings 242 or as a separate memory area, that defines values for a set of electrical stimulation parameters (e.g., a control stimulation parameter set) configured to elicit a detectable ECAP signal, such as a stimulation electrode combination, electrode polarity, current or voltage amplitude, pulse width, pulse rate, and pulse shape. ECAP test stimulation programs may also have additional information such as instructions regarding when to deliver control pulses based on the pulse width and/or frequency of the informed pulses defined in stimulation parameter settings 242.

Electrode impedance data 240 may include information indicative of the electrode impedance values of electrodes 232, 234 on leads 230A, 230B, respectively. Electrode impedance data 240 may include unipolar or bipolar impedances. In examples where the impedances are bipolar, electrode impedance data 240 may also include impedances across leads 230A, 230B (e.g., impedance between one of electrodes 232 and one of electrodes 234).

Stimulation generation circuitry 202 generates electrical stimulation signals in accordance with the electrical stimulation parameters noted above. Other ranges of stimulation parameter values may also be useful and may depend on the target stimulation site within patient 105. While stimulation pulses are described, stimulation signals may be of any form, such as continuous-time signals (e.g., sine waves) or the like.

Sensing circuitry 206 is configured to monitor signals from any combination of electrodes 232, 234. In some examples, sensing circuitry 206 includes one or more amplifiers, filters, and analog-to-digital converters. Sensing circuitry 206 may be used to sense physiological signals, such as ECAP signals. In some examples, sensing circuitry 206 detects ECAPs from a particular combination of electrodes 232, 234. In some cases, the particular combination of electrodes fir sensing ECAPs includes different electrodes than a set of electrodes 232, 234 used to deliver stimulation pulses. Alternatively, in other cases, the particular combination of electrodes used for sensing ECAPs includes at least one of the same electrodes as a set of electrodes used to deliver stimulation pulses to patient 105. Sensing circuitry 206 may provide signals to an analog-to-digital converter, for conversion into a digital signal for processing, analysis, storage, or output by processing circuitry 210.

In one or more examples described in this disclosure, processing circuitry 210 may utilize electrode impedance data 240 to determine from which electrodes sensing circuitry 206 is to monitor signals for sensing signals, such as ECAP signals. For instance, electrodes 232, 234 having relatively higher electrode impedance values as compared to other electrodes may be located under laminar bone, and therefore, may be well suited for sensing ECAP signals as the amplitude of the ECAP signals is likely to be highest for the electrodes of electrodes 232, 234 that are under the laminar bone. The electrodes 232, 234 used for sensing may be located on the same lead 230A, 230B or may be located across leads 230A, 230B.

Processing circuitry 210 may similarly determine which electrodes 232, 234 to utilize for outputting stimulation signals. For instance, electrodes 232, 234 having relatively higher electrode impedance values may be well suited for outputting stimulation because the stimulation signal is more likely to be directed towards spinal cord 120 due to the high resistance of the laminar bone. However, in cases, it may be possible that patient 105 does not prefer such focused therapy, in which case processing circuitry 210 may select another pair of electrodes 232, 234. The electrodes 232, 234 used for stimulating may be located on the same lead 230A, 230B or may be located across leads 230A, 230B.

In some examples, processing circuitry 210 may utilize the sensed ECAP signals to determine the stimulation signals. For instance, based on the ECAP signals, processing circuitry 210 may increase or decrease the stimulation amplitude, pulse width, or frequency. Accordingly, the ECAP signals may be part of a closed-loop therapy, in which processing circuitry 210 utilizes the ECAP signals to control the stimulation signal to provide efficacious therapy. For example, processing circuitry 210 may adjust stimulation amplitude, pulse width and/or frequency in response to ECAP signal characteristic such as ECAP amplitude.

Telemetry circuitry 208 supports wireless communication between IMD 200 and an external programmer (not shown in FIG. 2) or another computing device under the control of processing circuitry 210. Processing circuitry 210 of IMD 200 may receive, as updates to programs, values for various stimulation parameters such as amplitude and electrode combination, from the external programmer via, telemetry circuitry 208. Processing circuitry 210 may store updates to the stimulation parameter settings 242 or any other data in storage device 212. Telemetry circuitry 208 in IMD 200, as well as telemetry circuits in other devices and systems described herein, such as the external programmer, may accomplish communication by radiofrequency (RF) communication techniques. In addition, telemetry circuitry 208 may communicate with an external medical device programmer (not shown in FIG. 2) via proximal inductive interaction of IMD 200 with the external programmer. The external programmer may be one example of external programmer 150 of FIG. 1. Accordingly, telemetry circuitry 208 may send information to the external programmer on a continuous basis, at periodic intervals, or upon request from MID 110 or the external programmer.

Processing circuitry 210 may include any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processing circuitry 210 herein. Processing circuitry 210 controls stimulation generation circuitry 202 to generate stimulation signals according to stimulation parameter settings 242 and any other instructions stored in storage device 212 to apply stimulation parameter values specified by one or more of programs, such as amplitude, pulse width, pulse rate, and pulse shape of each of the stimulation signals.

In the example shown in FIG. 2, the set of electrodes 232 includes electrodes 232A, 232B, 232C, and 232D, and the set of electrodes 234 includes electrodes 234A, 234B, 234C, and 234D. In other examples, a single lead may include all eight electrodes 232 and 234 along a single axial length of the lead. In some examples, a single lead may include more than eight electrodes, such as 16 electrodes. Having leads with 16 electrodes may be beneficial as there is a higher likelihood that some electrodes will be under the laminar bone for stimulation and sensing.

Processing circuitry 210 also controls stimulation generation circuitry 202 to generate and apply the stimulation signals to selected combinations of electrodes 232, 234. Stimulation generation circuitry 202 includes a plurality of pairs of voltage sources, current sources, voltage sinks, or current sinks connected to each of electrodes 232, 234 such that each pair of electrodes has a unique signal circuit. In other words, in these examples, each of electrodes 232, 234 is independently controlled via its own signal circuit (e.g., via a combination of a regulated voltage source and sink or regulated current source and sink), as opposed to switching signals between electrodes 232, 234.

Electrodes 232, 234 on respective leads 230 may be constructed of a variety of different designs. For example, one or both of leads 230 may include one or more electrodes at each longitudinal location along the length of the lead, such as one electrode at different perimeter locations around the perimeter of the lead at each of the locations A, B, C, and D. In one example, the electrodes may be electrically coupled to stimulation generation circuitry 202 via respective wires that are straight or coiled within the body of the lead and run to a connector at the proximal end of the lead. In another example, each of the electrodes of the lead may be electrodes deposited on a thin film. The thin film may include an electrically conductive trace for each electrode that runs the length of the thin film to a proximal end connector. The thin film may then be wrapped (e.g., a helical wrap) around an internal member to form the lead 230. These and other constructions may be used, for example, to create a lead with a complex electrode geometry.

Although sensing circuitry 206 is incorporated into a common housing with stimulation generation circuitry 202 and processing circuitry 210 in FIG. 2, in other examples, sensing circuitry 206 may be in a separate housing from IMD 200 and may communicate with processing circuitry 210 via wired or wireless communication techniques. In some examples, one or more of electrodes 232 and 234 are suitable for sensing the ECAPs. For instance, electrodes 232 and 234 may sense the voltage amplitude of a portion of the ECAP signals, where the sensed voltage amplitude, such as the voltage difference between features within the signal, is a characteristic the ECAP signal. As described, in some examples, the electrodes 232 and 234 suitable for sensing ECAP signals may be implanted to be located under the laminar bone.

Storage device 212 may be configured to store information within IMD 200 during operation. Storage device 212 may include a computer-readable storage medium or computer-readable storage device. In some examples, storage device 212 includes one or more of a short-term memory or a long-term memory-. Storage device 212 may include, for example, random access memories (RAM), dynamic random access memories (DRAM), static random access memories (SRAM), magnetic discs, optical discs, flash memories, or forms of electrically programmable memories (EPROM) or electrically erasable and programmable memories (EEPROM). In some examples, storage device 212 is used to store data indicative of instructions for execution by processing circuitry 210.

As described, electrodes 232 and 234 may be the electrodes that sense the characteristic value of the ECAP signal. Sensor(s) 222 may include one or more accelerometers, optical sensors, chemical sensors, temperature sensors, pressure sensors, or any other types of sensors. Sensor(s) 222 may output patient parameter values that may be used as feedback to control delivery of therapy. For example, sensor(s) 222 may indicate patient activity or posture, and processing circuitry 210 may increase the frequency of control pulses and ECAP sensing in response to detecting increased patient activity or posture.

Power source 224 is configured to deliver operating power to the components of IMD 200. Power source 224 may include a battery and a power generation circuit to produce the operating power. In some examples, the battery is rechargeable to allow extended operation. In some examples, recharging is accomplished through proximal inductive interaction between an external charger and an inductive charging coil within IMD 200. Power source 224 may include any one or more of a plurality of different battery types, such as nickel cadmium batteries and lithium ion batteries.

Figure 3:
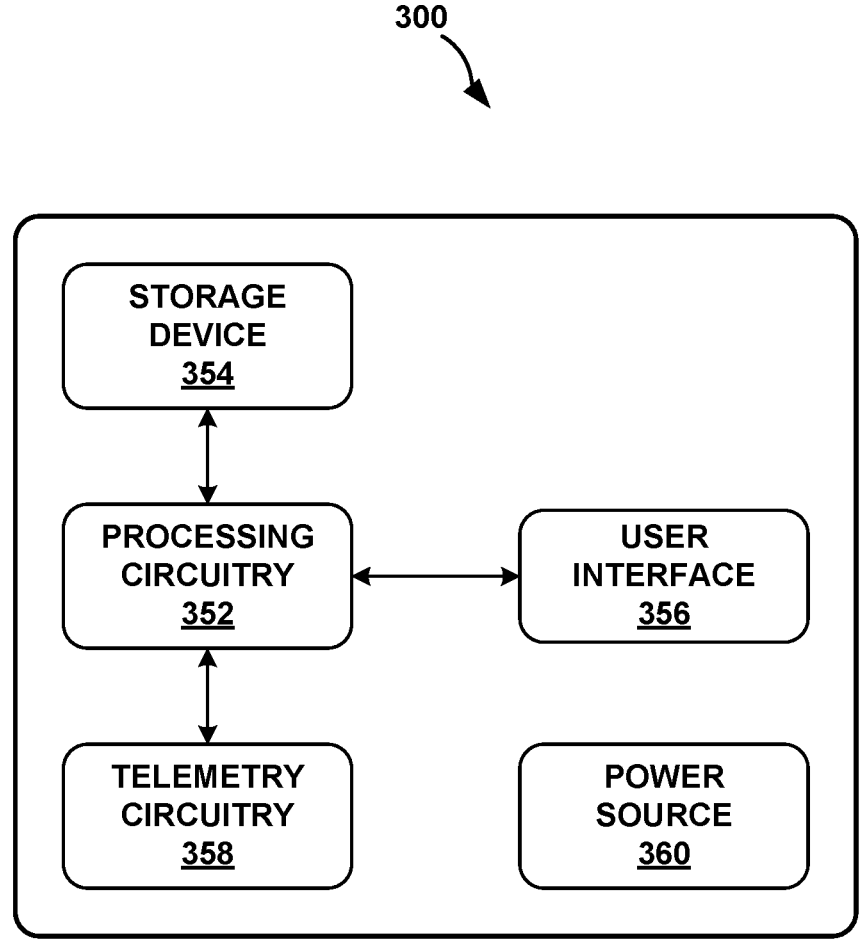
FIG. 3 is a block diagram illustrating an example configuration of components of an example external programmer, in accordance with one or more techniques of this disclosure.

FIG. 3 is a block diagram illustrating an example configuration of components of an example external programmer 300. External programmer 300 may be an example of external programmer 150 of FIG. 1. Although external programmer 300 may generally be described as a hand-held device, external programmer 300 may be a larger portable device or a more stationary device. In addition, in other examples, external programmer 300 may be included as part of an external charging device or include the functionality of an external charging device. As illustrated in FIG. 3, external programmer 300 may include processing circuitry 352, storage device 354, user interface 356, telemetry circuitry 358, and power source 360. Storage device 354 may store instructions that, when executed by processing circuitry 352, cause processing circuitry 352 and external programmer 300 to provide the functionality ascribed to external programmer 300 throughout this disclosure. Each of these components, circuitry, or modules, may include electrical circuitry that is configured to perform some, or all of the functionality described herein. For example, processing circuitry 352 may include processing circuitry configured to perform the processes discussed with respect to processing circuitry 352.

In general, external programmer 300 includes any suitable arrangement of hardware, alone or in combination with software and/or firmware, to perform the techniques attributed to external programmer 300, and processing circuitry 352, user interface 356, and telemetry circuitry 358 of external programmer 300. In various examples, external programmer 300 may include one or more processors, such as one or more microprocessors, DSPs, ASICs, FPGAs, or any other equivalent integrated or discrete logic circuitry, as well as any combinations of such components. External programmer 300 also, in various examples, may include a storage device 354, such as RAM, ROM, PROM, EPROM, EEPROM, flash memory, a hard disk, a CD-ROM, including executable instructions for causing the one or more processors to perform the actions attributed to them. Moreover, although processing circuitry 352 and telemetry circuitry 358 are described as separate modules, in some examples, processing circuitry 352 and telemetry circuitry 358 are functionally integrated. In some examples, processing circuitry 352 and telemetry circuitry 358 correspond to individual hardware units, such as ASICs, DSPs, FPGAs, or other hardware units.

Storage device 354 (e.g., a storage device may store instructions that, when executed by processing circuitry 352, cause processing circuitry 352 and external programmer 300 to provide the functionality ascribed to external programmer 300 throughout this disclosure. For example, storage device 354 may include instructions that cause processing circuitry 352 to obtain a parameter se from memory, select an electrode combination, or receive a user input and send a corresponding command to IMD 200, or instructions for any other functionality. In addition, storage device 354 may include a plurality of programs, where each program includes a parameter set that defines therapy stimulation or control stimulation. Storage device 354 may also store data received from a medical device (e.g., IMD 110).

User interface 356 may include a button or keypad, lights, a speaker for voice commands, a display, such as a liquid crystal (LCD), light-emitting diode (LED), or organic light-emitting diode (OLED). In some examples the display includes a touch screen. User interface 356 may be configured to display any information related to the delivery of electrical stimulation.

As one example, user interface 356 may output information indicative of an electrode impedance value for one or more electrodes of a lead. User interface 356 may provide an interface for the clinician to identify one or more electrodes (e.g., a group of electrodes) from the one or more electrodes for sensing a signal (e.g., ECAP signal) based on the electrode impedance value for the one or more electrodes. The group of one or more electrodes may include electrodes having electrode impedance values that are greater than electrode impedance values of other electrodes on the lead. User interface 356 may also provide an interface for the clinician to select one or more electrodes from the identified electrodes to sense the signal. The electrodes in the group of electrodes may be likely to be under bone (e.g., under laminar bone) because the electrode impedance value of the electrodes in the group of electrodes is higher than the electrode impedance value of the other electrodes. In some examples, the processing circuitry may identify the group of electrodes based on all electrodes in the group having an impedance greater than or equal to a threshold impedance. In some examples, the processing circuitry may identify the group of electrodes based on relative impedances of the electrodes (e.g., the group may include electrodes having higher impedance relative to other electrodes).

Telemetry circuitry 358 may support wireless communication between the medical device and external programmer 300 under the control of processing circuitry 352. Telemetry circuitry 358 may also be configured to communicate with another computing device via wireless communication techniques, or direct communication through a wired connection. In some examples, telemetry circuitry 358 provides wireless communication via an RF or proximal inductive medium. In some examples, telemetry circuitry 358 includes an antenna, which may take on a variety of forms, such as an internal or external antenna.

Examples of local wireless communication techniques that may be employed to facilitate communication between external programmer 300 and MID 110 include RF communication according to the 802.11 or Bluetooth® specification sets or other standard or proprietary telemetry protocols. In this manner, other external devices may be capable of communicating with external programmer 300 without needing to establish a secure wireless connection.

In some examples, selection of stimulation parameters or therapy stimulation programs are transmitted to the medical device for delivery to a patient (e.g., patient 105 of FIG. 1). In other examples, the therapy may include medication, activities, or other instructions that patient 105 must perform themselves or a caregiver perform for patient 105. In some examples, external programmer 300 provides visual, audible, and/or tactile notifications that indicate there are new instructions. External programmer 300 requires receiving user input acknowledging that the instructions have been completed in some examples.

User interface 356 of external programmer 300 may also be configured to receive an indication from a clinician instructing a processor of the medical device to update one or more therapy stimulation programs in response to an indication that the leads have migrated. For example, user interface 356 may receive an indication from the clinician to adjust a pulse width and/or an amplitude of the stimulation parameter values to compensate for the migration of the leads. User interface 356 may also receive instructions from the clinician commanding any electrical stimulation, including therapy stimulation (e.g., to provide therapy) and control pulses (e.g., to evoke a compound action potential) to commence or to cease.

Power source 360 is configured to deliver operating power to the components of external programmer 300. Power source 360 may include a battery and a power generation circuit to produce the operating power. In some examples, the battery is rechargeable to allow extended operation. Recharging may be accomplished by electrically coupling power source 360 to a cradle or plug that is connected to an alternating current (AC) outlet. In addition, recharging may be accomplished through proximal inductive interaction between an external charger and an inductive charging coil within external programmer 300. In other examples, traditional batteries (e.g., nickel cadmium or lithium ion batteries) may be used. In addition, external programmer 300 may be directly coupled to an alternating current outlet to operate.

The architecture of external programmer 300 illustrated in FIG. 3 is shown as an example. The techniques as set forth in this disclosure may be implemented in the example external programmer 300 of FIG. 3, as well as other types of systems not described specifically herein, Nothing in this disclosure should be construed so as to limit the techniques of this disclosure to the example architecture illustrated by FIG. 3.

Figure 4:
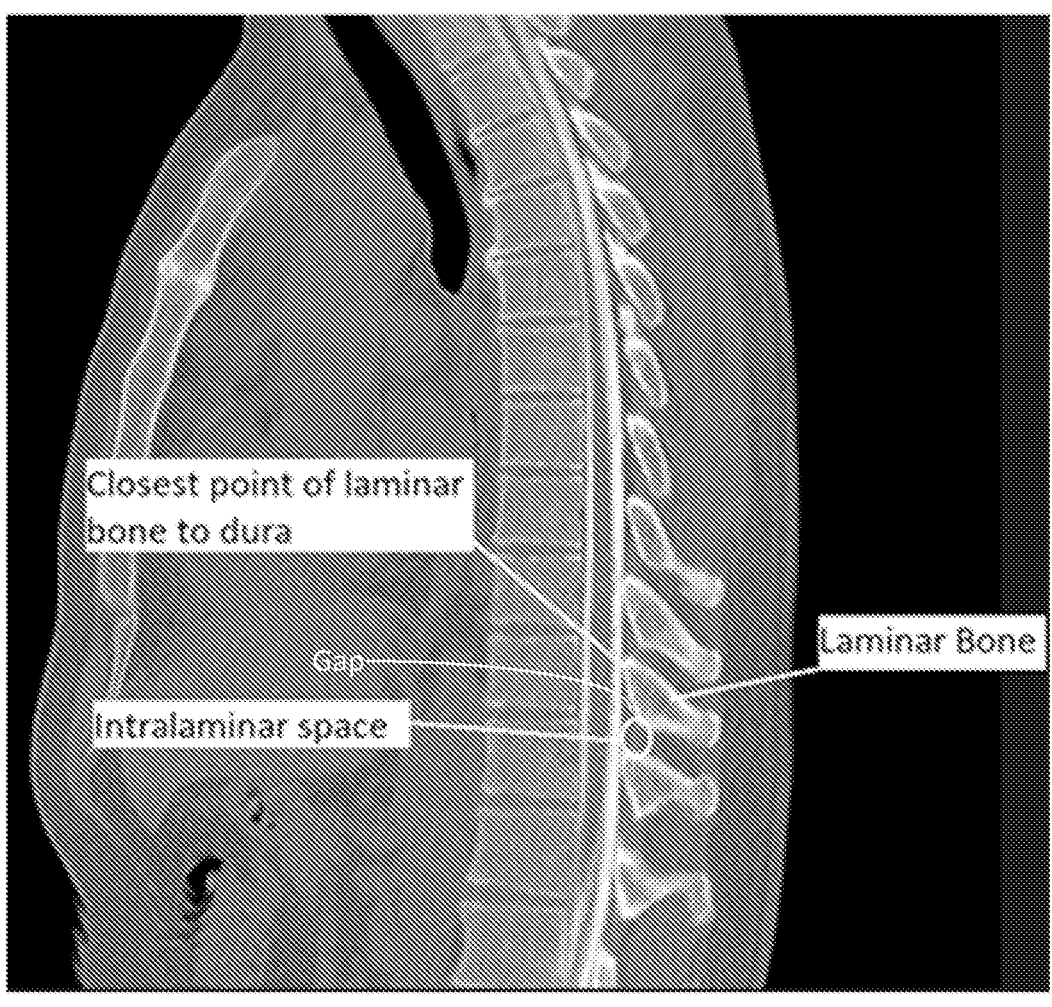
FIG. 4 is a sagittal slice of the human body illustrating the laminar bone and other relevant structures associated with the spine.

FIG. 4 is an illustration showing the laminar bone. FIG. 4 shows a sagittal image from a thoracic CT scan that shows the relationship of the laminar bone with respect to the spinal canal. For instance, FIG. 4 illustrates a plurality of laminar bones, and one of the laminar hones is referenced. In some cases, the nerve roots enter the spinal cord 120 in between the bony structures and identifying these anatomical landmarks via non-imaging automatic (potentially at home) measures may be desirable.

As illustrated, the laminar hone attaches to the spinal cord 120 at an angle. For an electrode that is under the location identified as the closest point of laminar bone to dura, the electrode impedance value of such an electrode would be greater than the electrode impedance value of an electrode in the area located the gap or in the intralaminar space. The electrode impedance value of an electrode that is on spinal cord 120 but located in the region referred to as the gap (e.g., still under the laminar bone but not at the point where the laminar bone attaches to spina cord 12) may be greater than the electrode impedance value of an electrode in the intralaminar space but less than the electrode impedance value of an electrode under the "closest point of laminar hone to dura." The electrode impedance value of an electrode in the intralaminar space may the lowest. As described above, the electrode impedance value of an electrode may refer to unipolar electrode impedance value (e.g., between electrode and indifferent electrode) or bipolar electrode impedance value (e.g., between electrode and another electrode on same lead or on different leads).

Figures 5A, 5B:
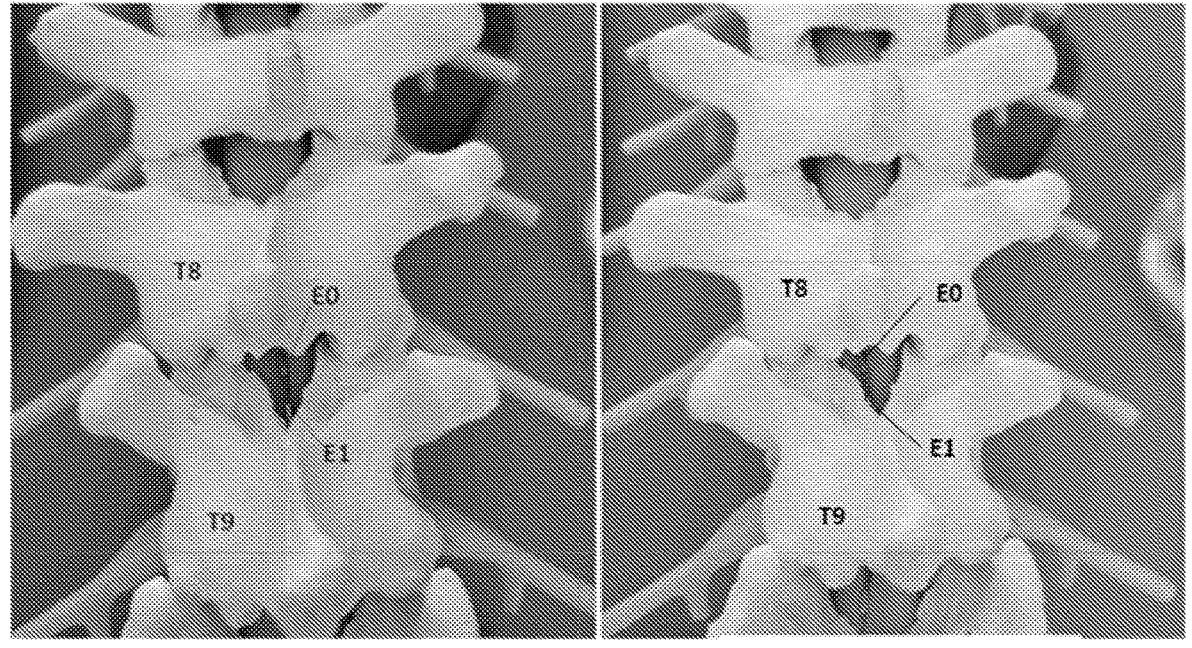
FIGS. 5A and 5B are conceptual diagrams illustrating examples of positioning of electrodes.

FIGS. 5A and 5B are conceptual diagrams illustrating examples of positioning of electrodes. In FIG. 5A, a 1×8 percutaneous SCS lead is shown placed midline. Electrodes E0/E1 are visible in the intralaminar space between T8 and T9. In FIG. 5B, the lead is moved slightly lateral and E1 is now situated underneath the rostral edge of the T9 laminar bone. In general, visualizing the position of the laminar bone and electrodes in vivo is more challenging than in the anatomical model shown above.

Electrode E1 is under the T9 laminar bone in the sense that if the patient is lying prone, the electrode E1 is lying in the epidural space on the dorsal side of the spinal cord, and the laminar bone T9 is dorsal to electrode E1 and partially or fully covering the electrode. Electrode E0 between bones may mean that if the patient is lying prone, electrode E0 is lying in the epidural space, and there is no laminar bone that is fully dorsal to the electrode (e.g., laminar bone T8 and T9 are not fully covering electrode E0).

Figure 6:
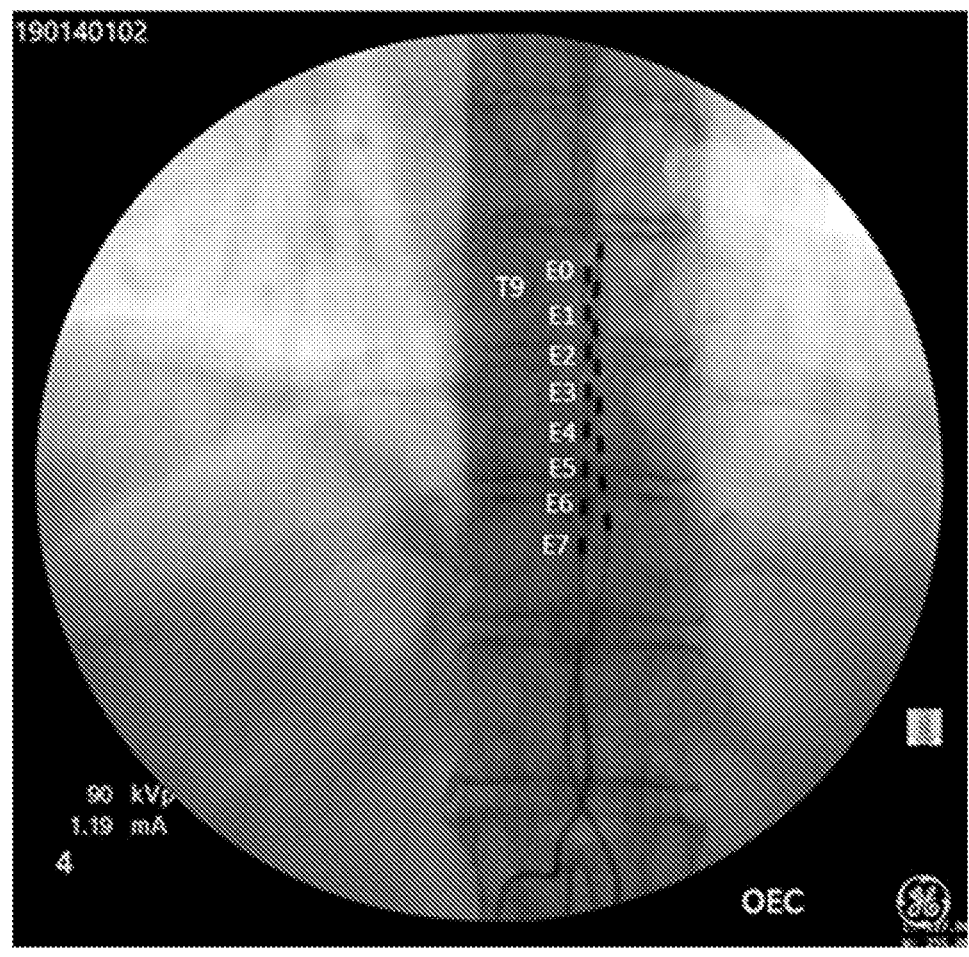
FIG. 6 is an image showing percutaneous spinal cord stimulation leads implanted in the epidural space of the spinal cord.

FIG. 6 is an image showing leads implanted in a spine. FIG. 6 illustrates an anterior/posterior fluorograph of two leads in patient 105. Fluorography is the standard imaging tool used during lead placement. While the pedicles, intervertebral discs, and spinous processes may be seen to some degree, the boundary between the laminar bone and intralaminar space cannot be appreciated.

Accordingly, this disclosure describes example techniques to assess electrode location relative to the laminar bone to assist in electrode programming. Lead impedance may be employed in this regard. In the example above, electrode impedance values relative to an indifferent electrode (e.g., electrode not on lead, such as an anode on a case of IMD 110) in the body may be as follows. The following is merely an example of impedance values to assist with understanding.

| | E0 | E1 | E2 | E3 | E4 | E5 | E6 | E7 |
|---|---|---|---|---|---|---|---|---|
| Impedance | 925 | 1100 | 1020 | 875 | 1150 | 1060 | 980 | 1200 |

The relatively higher impedances above are indicative of electrode placement under the laminar bone. By means of example, assume a patient has good therapy with a stimulation bipole at E0+/E1– and the clinician is tasked with allocating either E5/E6 or E6/E7 for ECAP sensing. As E7 has the strongest effect from the laminar bone, as indicated by the relatively high value of the sensed impedance, the E6/E7 pair is selected.

Conversely, a clinician notes equivalent therapeutic outcome with stimulation on E0–/E1+ and E1–/E2+. E1–/E2+ is selected because the shielding and mass effect of the laminar bone (as reflected in the higher impedances) results in lower stimulation amplitude thresholds and stimulation artifact, which eases ECAP sensing.

In addition, impedance can be measured relative to other electrodes on the same lead (E0-E1, E0-E2, etc.) or on the second lead (E0-E8, E0-E9, etc.). Doing this quickly and automatically provides an impedance map (e.g., electrode impedance data 240 of FIG. 2) of where electrodes of those leads are located within the neural anatomy and relative to each other. This will also be impacted by positional changes as the epidural space changes depending on the position of the spinal column. Combining lead impedance measurements and ECAP measurements, with input from the orientation/accelerometer embedded in IMD 110 could help track changes over time with different postures or activities and aid in the selection of optimal electrodes for stimulation and recording.

FIG. 7 is a flowchart of an example method for electrode selection, in accordance with one or more techniques of this disclosure. Fax ease, the example of FIG. 7 is described with respect to processing circuitry 210 of FIG. 2.

Processing circuitry 210 may determine an electrode impedance value for one or more electrodes 232, 234 of lead 230A, 230B coupled to IMD 110 (700). Processing circuitry 210 may store the electrode impedance value as electrode impedance data 240. Processing circuitry 210 may be configured to determine at least one of a first bipolar electrode impedance value for the one or more electrodes of the lead, where the first bipolar electrode impedance value is an impedance between two or more electrodes on the lead, a second bipolar electrode impedance value for the one or more electrodes, where the second bipolar electrode impedance value is determined based on an impedance between one of the electrodes on the lead and an electrode on another lead, or a unipolar electrode impedance value for the one or more electrodes, where the unipolar electrode impedance value is an impedance between the one or more electrodes on a lead and an indifferent electrode that is not on the lead (e.g., such as an anode on an IMD case).

Processing circuitry 210 may identify one or more electrodes of the lead having electrode impedance values that are greater than electrode impedance value of other electrodes on the lead (702). The one or more electrodes may be a group of one or more electrodes. For example, to identify the one or more electrodes (e.g., group of electrodes), processing circuitry 210 may be configured to determine pairs of electrodes that have a greater impedance than other pairs of the electrodes.

From the determined group of one or more electrodes, processing circuitry 210 may determine a recommendation of electrodes to use for sensing a signal (704). For example, processing circuitry 210 may be configured to determine which electrodes in the determined group are near a proximal or distal end of the lead. To determine the recommendation of electrodes, processing circuitry 210 may be configured to determine the recommendation based on the determination of which electrodes in the determined group are near the proximal or distal end of the lead.

Processing circuitry 210 may output information indicative of the recommendation (706). In some examples, processing circuitry 210 may be configured to determine a recommendation of electrodes to use for stimulation based on the electrode impedance value (and in some examples based on the sensed signal), and output information indicative of the recommendation of electrodes to use for stimulation.

FIG. 8 is a flowchart of another example method for electrode selection, in accordance with one or more techniques of this disclosure. A clinician (e.g., via programmer 300) may receive information indicative of an electrode impedance value for one or more electrodes of a lead (800). The clinician (e.g., via programmer 300) may identify one or more electrodes from the one or more electrodes for sensing a signal based on the electrode impedance value for the one or more electrodes, wherein the identified electrodes include electrodes having electrode impedance values that are greater than electrode impedance values of other electrodes on the lead (802). For instance, there may be threshold value (e.g., based on average of impedances) and electrodes having impedance greater than the threshold may belong to the group, or electrodes having impedance greater than some threshold regardless of how determined. There may be other ways to identify the group and the techniques are not limited. The clinician (e.g., via programmer 300) may select one or more of the identified electrodes sense the signal (804).

FIGS. 9A and 9B are conceptual diagrams illustrating anatomical directionality. For instance, leads 230A and 230B may be implanted medially along the spine of patient 105. As illustrated in FIG. 9A, medially may mean that leads 230A and 230B are implanted centered to the spine, similar to FIG. 6.

FIG. 9B illustrates the ventral and dorsal directions. In one or more examples, leads 230A, 230B may be implanted such as one or more of electrodes 232, 234 are ventral to the laminar bone, and dorsal to the spinal cord, where FIG. 9B illustrates examples of the ventral and dorsal directions. For instance, an electrode that is under the laminar bone may be lying the epidural space that is dorsal to the spinal cord, but ventral to the laminar bone. An electrode that is intralaminar or between bones may mean that the electrode is lying in the epidural space, and there is no laminar bone that is fully dorsal to the electrode.

The following examples are described herein. The examples may be used together or separately.

Example 1: A medical device includes processing circuitry configured to determine an electrode impedance value for each of one or more electrodes of a lead coupled to the medical device; identify one or more of the electrodes having electrode impedance values that are greater than electrode impedance values of other electrodes of the lead; from the identified one or more electrodes, determine a recommendation of electrodes to use for sensing a signal; and output information indicative of the recommendation.

Example 2: The medical device of example 1, wherein the signal is an evoked compound action potential (ECAP) signal of the patient.

Example 3: The medical device of any of examples 1 and 2, wherein at least one of the recommended electrodes is under a laminar bone of the patient.

Example 4: The medical device of any of examples 1-3, wherein to determine the electrode impedance, the processing circuitry is configured to determine at least one of: a first bipolar electrode impedance value for the one or more electrodes, wherein the first bipolar electrode impedance value is determined based on an impedance between electrodes on the lead, a second bipolar electrode impedance value for the one or more electrodes, wherein the second bipolar electrode impedance value is determined based on an impedance between an electrode on the lead and an electrode on another lead, or a unipolar electrode impedance value for the one or more electrodes, wherein the unipolar electrode impedance value is determined based on an impedance between the one or more electrodes and an indifferent electrode that is not on the lead.

Example 5: The medical device of any of examples 1-4, wherein to identify the one or more electrodes, the processing circuitry is configured to determine electrode pairs that have a greater impedance than other pairs of electrodes.

Example 6: The medical device of any of examples 1-5, wherein the processing circuitry is configured to determine which of the identified electrodes are near a proximal or distal end of the lead, and wherein to determine the recommendation of electrodes, the processing circuitry is configured to determine the recommendation based on the determination of which of the identified electrodes are near the proximal or distal end of the lead.

Example 7: The medical device of any of examples 1-6, wherein the processing circuitry is configured to determine a recommendation of electrodes to use for stimulation based on the electrode impedance value.

Example 8: The medical device of any of examples 1-7, wherein the processing circuitry is configured to determine a recommendation of electrodes to use for stimulation based on the electrode impedance value and the sensed signal.

Example 9: A method for selecting sensing electrodes includes receiving information indicative of an electrode impedance value for one or more electrodes of a lead; identifying one or more electrodes from the one or more electrodes for sensing a signal based on the electrode impedance value for the one or more electrodes, wherein the identified electrodes include electrodes having electrode impedance values that are greater than electrode impedance values of other electrodes on the lead; and selecting one or more of the identified electrodes to sense the signal.

Example 10: The method of example 9, wherein the signal is an evoked compound action potential (ECAP) signal.

Example 11: The method of any of examples 9 and 10, wherein selecting the one or more electrodes selecting the one or more of the identified electrodes that are on a proximal or distal end of the lead.

Example 12: A method includes determining an electrode impedance value for each of one or more electrodes of a lead coupled to the medical device; identifying one or more of the electrodes having electrode impedance values that are greater than electrode impedance values of other electrodes of the lead; from the identified one or more electrodes, determining a recommendation of electrodes to use for sensing a signal; and outputting information indicative of the recommendation.

Example 13: The method of example 12, wherein the signal is an evoked compound action potential (ECAP) signal of the patient.

Example 14: The method of any of examples 12 and 13, wherein at least one of the recommended electrodes is under a laminar bone of the patient.

Example 15: The method of any of examples 12-14, wherein determining the electrode impedance comprises determining at least one of: a first bipolar electrode impedance value for the one or more electrodes, wherein the first bipolar electrode impedance value is determined based on an impedance between electrodes on the lead, a second bipolar electrode impedance value for the one or more electrodes, wherein the second bipolar electrode impedance value is determined based on an impedance between an electrode on the lead and an electrode on another lead, or a unipolar electrode impedance value for the one or more electrodes, wherein the unipolar electrode impedance value is determined based on an impedance between the one or more electrodes and an indifferent electrode that is not on the lead.

Example 16: The method of any of examples 12-15, wherein identifying the one or more electrodes comprises determining electrode pairs that have a greater impedance than other pairs of electrodes.

Example 17: The method of any of examples 12-16, further comprising determining which of the identified electrodes are near a proximal or distal end of the lead, and wherein determining the recommendation of electrodes comprises determining the recommendation based on the determination of which of the identified electrodes are near the proximal or distal end of the lead.

Example 18: The method of any of examples 12-17, further comprising determining a recommendation of electrodes to use for stimulation based on the electrode impedance value.

Example 19: The method of any of examples 12-18, further comprising determine a recommendation of electrodes to use for stimulation based on the electrode impedance value and the sensed signal.

Example 20: A computer readable storage medium having instructions stored thereon that when executed cause one or more processors to perform the method of any one or combination of examples 12-19.

The techniques described in this disclosure may be implemented, at least in part, in hardware, software, firmware or any combination thereof. For example, various aspects of the described techniques may be implemented within one or more processors or processing circuitry, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also perform one or more of the techniques of this disclosure.

Such hardware, software, and firmware may be implemented within the same device or within separate devices to support the various operations and functions described in this disclosure. In addition, any of the described units, circuits or components may be implemented together or separately as discrete but interoperable logic devices. Depiction of different features as circuits or units is intended to highlight different functional aspects and does not necessarily imply that such circuits or units must be realized by separate hardware or software components. Rather, functionality associated with one or more circuits or units may be performed by separate hardware or software components or integrated within common or separate hardware or software components.

The techniques described in this disclosure may also be embodied or encoded in a computer-readable medium, such as a computer-readable storage medium, containing instructions that may be described as non-transitory media. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

What is claimed is:

1. A medical device comprising:
   processing circuitry configured to:
   determine an electrode impedance value for each of a plurality of electrodes of a lead coupled to the medical device;
   identify a subset of one or more electrodes from the plurality of electrodes, the subset of one or more electrodes of the lead having electrode impedance values that are greater than electrode impedance values of other electrodes of the lead that are not in the subset;
   determine a recommendation of one or more electrodes from the subset of one or more electrodes to use for sensing a signal subsequent to placement of the lead; and
   output information indicative of the recommendation.

2. The medical device of claim 1, wherein the signal is an evoked compound action potential (ECAP) signal of a patient.

3. The medical device of claim 1, wherein at least one of the recommended electrodes is configured to be under a laminar bone of a patient.

4. The medical device of claim 1, wherein to determine the electrode impedance value, the processing circuitry is configured to determine at least one of:
   a first bipolar electrode impedance value for the plurality of electrodes of the lead, wherein the first bipolar electrode impedance value is determined based on an impedance between two or more electrodes of the lead,
   a second bipolar electrode impedance value for the plurality of electrodes of the lead, wherein the second bipolar electrode impedance value is determined based on an impedance between one of the electrodes of the lead and an electrode of another lead, or
   a unipolar electrode impedance value for the plurality of electrodes of the lead, wherein the unipolar electrode impedance value is determined based on an impedance between the one or more electrodes of the lead and an indifferent electrode that is not on the lead.

5. The medical device of claim 1, wherein to identify the subset of one or more electrodes, the processing circuitry is configured to determine pairs of the electrodes that have a greater impedance than other pairs of the electrodes.

6. The medical device of claim 1, wherein the processing circuitry is configured to determine which electrodes of the subset of one or more electrodes are near a proximal or distal end of the lead, and wherein to determine the recommendation of one or more electrodes from the subset of one or more electrodes, the processing circuitry is configured to determine the recommendation based on the determination of which electrodes of the subset of one or more electrodes are near the proximal or distal end of the lead.

7. The medical device of claim 1, wherein the processing circuitry is configured to determine a recommendation of electrodes to use for stimulation based on the electrode impedance value.

8. The medical device of claim 1, wherein the processing circuitry is configured to determine a recommendation of electrodes to use for stimulation based on the electrode impedance value and the signal sensed by the one or more electrodes recommended to use for sensing the signal.

9. The medical device of claim 1, wherein at least one electrode of the subset of electrodes is located in a dorsal epidural space of a spine, and a laminar bone is dorsal to the at least one electrode and partially or fully covering the electrode.

10. A method comprising:
   determining an electrode impedance value for each of a plurality of electrodes of a lead coupled to a medical device;
   identifying a subset of one or more electrodes from the plurality of electrodes, the subset of one or more electrodes of the lead having electrode impedance values that are greater than electrode impedance values of other electrodes of the lead that are not in the subset;
   determining a recommendation of one or more electrodes from the subset of one or more electrodes to use for sensing a signal subsequent to placement of the lead; and
   outputting information indicative of the recommendation.

11. The method of claim 10, wherein the signal is an evoked compound action potential (ECAP) signal of a patient.

12. The method of claim 10, wherein at least one of the recommended electrodes is configured to be under a laminar bone of a patient.

13. The method of claim 10, wherein identifying the subset of one or more electrodes comprises determining pairs of the electrodes that have a greater impedance than other pairs of the electrodes.

14. The method of claim 10, further comprising determining which electrodes of the subset of one or more electrodes are near a proximal or distal end of the lead, and wherein determining the recommendation of one or more electrodes from the subset of one or more electrodes comprises determining the recommendation based on the determination of which electrodes of the subset of one or more electrodes are near the proximal or distal end of the lead.

15. The method of claim 10, further comprising determining a recommendation of electrodes to use for stimulation based at least in part on (1) the electrode impedance value or (2) the electrode impedance value and the sensed signal.

16. The method of claim 10, wherein determining the electrode impedance comprises determining at least one of:
   a first bipolar electrode impedance value for the plurality of electrodes, wherein the first bipolar electrode impedance value is determined based on an impedance between electrodes on the lead,
   a second bipolar electrode impedance value for the plurality of electrodes, wherein the second bipolar electrode impedance value is determined based on an impedance between an electrode on the lead and an electrode on another lead, or a unipolar electrode impedance value for the plurality of electrodes, wherein the unipolar electrode impedance value is determined based on an impedance between the one or more electrodes and an indifferent electrode that is not on the lead.

17. A method for selecting sensing electrodes, the method comprising:

receiving information indicative of an electrode impedance value for a plurality of electrodes of a lead;

identifying a subset of one or more electrodes from the plurality of electrodes for sensing a signal based on the electrode impedance value for the plurality of electrodes, wherein the identified subset of one or more electrodes include electrodes having electrode impedance values that are greater than electrode impedance values of other electrodes on the lead that are not in the subset; and selecting one or more electrodes from the subset of one or more electrodes to sense the signal subsequent to placement of the lead.

18. The method of claim 17, wherein the signal is an evoked compound action potential (ECAP) signal.

19. The method of claim 17, wherein selecting the one or more electrodes from the subset of one or more electrodes comprises selecting the one or more electrodes of the subset of one or more electrodes that are on a proximal or distal end of the lead.

20. A computer readable storage medium having instructions stored thereon that when executed cause one or more processors to:

determine an electrode impedance value for each of a plurality of electrodes of a lead coupled to a medical device;

identify a subset of one or more electrodes from the plurality of electrodes, the subset of one or more electrodes of the lead having electrode impedance values that are greater than electrode impedance values of other electrodes of the lead that are not in the subset;

determine a recommendation of one or more electrodes from the subset of one or more electrodes to use for sensing a signal subsequent to placement of the lead; and output information indicative of the recommendation.

21. The computer-readable storage medium of claim 20, wherein one or more of:

the signal is an evoked compound action potential (ECAP) signal of a patient;

at least one of the recommended electrodes is configured to be under a laminar bone of a patient;

the instructions that cause the one or more processors to identify the subset of one or more electrodes comprise instructions that cause the one or more processors to determine pairs of the electrodes that have a greater impedance than other pairs of the electrodes; and the instructions that cause the one or more processors to determine the recommendation of one or more electrodes comprise instructions that cause the one or more processors to determine the recommendation based on a determination of which electrodes of the subset of one or more electrodes are near the proximal or distal end of the lead.

* * * * *